US012595456B2

(12) United States Patent
Saito et al.

(10) Patent No.: US 12,595,456 B2
(45) Date of Patent: *Apr. 7, 2026

(54) CELL OBSERVATION DEVICE, ELECTROSTIMULATION DEVICE, AND CELL OBSERVATION METHOD

(71) Applicant: HAMAMATSU PHOTONICS K.K., Hamamatsu (JP)

(72) Inventors: Natsumi Saito, Hamamatsu (JP); Taira Ito, Hamamatsu (JP); Takuji Kataoka, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 968 days.

This patent is subject to a terminal disclaimer.

(21) Appl. No.: 17/565,929

(22) Filed: Dec. 30, 2021

(65) Prior Publication Data

US 2022/0119756 A1 Apr. 21, 2022

Related U.S. Application Data

(63) Continuation of application No. 16/527,423, filed on Jul. 31, 2019, now Pat. No. 11,248,202, which is a
(Continued)

(30) Foreign Application Priority Data

Jan. 16, 2014 (JP) ................................. 2014-005990

(51) Int. Cl.
*C12M 1/34* (2006.01)
*C12M 1/42* (2006.01)
(Continued)

(52) U.S. Cl.
CPC ............ *C12M 35/02* (2013.01); *C12M 41/36* (2013.01); *C12N 13/00* (2013.01);
(Continued)

(58) Field of Classification Search
CPC ....... C12M 35/02; C12M 41/36; C12N 13/00; G01N 21/6452; G01N 27/416; G01N 33/4836; G01N 33/48707; G01N 33/48728
See application file for complete search history.

(56) References Cited

U.S. PATENT DOCUMENTS 3,065,156 A 11/1962 Thompson
4,295,854 A 10/1981 Huber
(Continued)

FOREIGN PATENT DOCUMENTS

JP S63-276478 A 11/1988
JP H9-196936 A 7/1997
(Continued)

OTHER PUBLICATIONS

International Preliminary Report on Patentability dated Jul. 28, 2016 for PCT/JP2014/079964.
(Continued)

*Primary Examiner* — Liban M Hassan
(74) *Attorney, Agent, or Firm* — Faegre Drinker Biddle & Reath LLP

(57) ABSTRACT

A cell observation device is cell observation device for observing a cell held by a microplate having a well holding a sample including the cell and includes a microplate holder for holding the microplate thereon, an electrical stimulation unit including an electrode pair including a first electrode and a second electrode, and a position controller for controlling a position of the electrical stimulation unit in a state in which the first electrode is disposed closer to the center of the well than the second electrode when the electrode pair is disposed in the well of the microplate. The tip of the first electrode extends more than the tip of the second electrode.

6 Claims, 24 Drawing Sheets

Related U.S. Application Data continuation of application No. 15/110,678, filed as application No. PCT/JP2014/079964 on Nov. 12, 2014, now Pat. No. 10,415,010.

(51) Int. Cl.

| | |
|---|---|
| *C12N 13/00* | (2006.01) |
| *G01N 21/64* | (2006.01) |
| *G01N 27/416* | (2006.01) |
| *G01N 33/483* | (2006.01) |
| *G01N 33/487* | (2006.01) |

(52) U.S. Cl.
CPC ....... *G01N 21/6452* (2013.01); *G01N 27/416* (2013.01); *G01N 33/4836* (2013.01); *G01N 33/48707* (2013.01); *G01N 33/48728* (2013.01)

(56) References Cited

U.S. PATENT DOCUMENTS

| | | | |
|---|---|---|---|
| 7,148,059 B1 | 12/2006 | Tillotson et al. | |
| 2004/0110123 A1 | 6/2004 | Maher et al. | |
| 2004/0210036 A1 | 10/2004 | Dwyer et al. | |
| 2005/0090005 A1 | 4/2005 | Kojima et al. | |
| 2005/0164161 A1 | 7/2005 | Augustine et al. | |
| 2006/0008906 A1 | 1/2006 | Wills et al. | |
| 2007/0004025 A1 | 1/2007 | Chen et al. | |
| 2011/0045959 A1* | 2/2011 | Kurihara ................ | C12M 47/02 |
| | | | 494/10 |

| | | | | |
|---|---|---|---|---|
| 2011/0262958 A1* | 10/2011 | Yasuda | .............. | G01N 33/5014 |
| | | | | 435/287.1 |
| 2012/0053084 A1 | 3/2012 | Gerber et al. | | |
| 2015/0276599 A1* | 10/2015 | Kataoka | ............. | G01N 33/5005 |
| | | | | 435/283.1 |
| 2015/0276708 A1* | 10/2015 | Kataoka | ............. | G01N 21/6452 |
| | | | | 435/29 |

FOREIGN PATENT DOCUMENTS

| | | | |
|---|---|---|---|
| JP | 2001-188044 A | 7/2001 | |
| JP | 2004-147517 A | 5/2004 | |
| JP | 2005-514909 A | 5/2005 | |
| JP | 2005-151807 | 6/2005 | |
| JP | 2005-204624 A | 8/2005 | |
| JP | 2005-261323 A | 9/2005 | |
| JP | 2011-188830 | 9/2011 | |
| JP | 2012-501646 A | 1/2012 | |
| JP | 2012-110327 A | 6/2012 | |
| WO | WO 97/49987 A1 | 12/1997 | |
| WO | WO 03/095620 A2 | 11/2003 | |
| WO | WO 2004/092363 A1 | 10/2004 | |

OTHER PUBLICATIONS

Papke, R., et al., "Working with OpusXpress: Methods for high volume oocyte experiments", Methods, 2010, vol. 51, pp. 121-133, (Year: 2010).

Mizuguchi, Yoshi Nori, "English machine translation of Japanese document JP-2001188044-A". (Year: 2001).

\* cited by examiner (a)

(b)

(a)

(b)

(a)

(b)

(a)

(b)

(a)

(b)

(a)

(b)

(a)

(b)

(a)

(b)

(a)

(b)

CELL OBSERVATION DEVICE, ELECTROSTIMULATION DEVICE, AND CELL OBSERVATION METHOD

TECHNICAL FIELD

The present invention relates to a cell observation device, an electrical stimulation device, and a cell observation method for observing a reaction of a sample including a cell to electrical stimulation.

BACKGROUND ART

In the field of drug discovery screening, influence of a drug administered to a sample of cells or the like is evaluated by measuring light emitted from the cells in certain cases. Patent Literature 1 discloses a measurement device that monitors a biological response of cells to electric-field stimulation by fluorescence detection. This measurement device employs a configuration in which an electrode pair of a coaxial cable shape or a parallel flat plate shape including a positive electrode and a negative electrode can be located in each of wells in which the cells are placed. Patent Literature 2 discloses a measurement device that treats a membrane potential of a cell through the use of electrical stimulation. This measurement device includes an electrode pair of two parallel electrodes for generating an electric field in an observation area of a well.

CITATION LIST

Patent Literature

Patent Literature 1: Japanese Unexamined Patent Publication No. 2005-514909
Patent Literature 2: Japanese Unexamined Patent Publication No. 2012-110327

SUMMARY OF INVENTION

Technical Problem

In general, a microplate in which cells to be observed are arranged has a shape in which the bottom of each well is flat, but a microplate having a shape in which the bottom of each well is concave such as U-shaped has been recently used. When the microplate having such a shape is used, the measurement device described in Patent Literature 1 or Patent Literature 2 employs the electrode pair of a coaxial cable shape or the parallel electrodes and thus is likely to have difficulty in appropriately applying electrical stimulation to cells placed in the wells.

Therefore, the present invention has been accomplished in view of the above-mentioned problem and it is an object of the present invention to provide a cell observation device, an electrical stimulation device, and a cell observation method that can appropriately apply electrical stimulation to a cell placed in a holding unit.

Solution to Problem

The inventors of the present application found that a positional relationship of electrode pairs was important when electrical stimulation was applied to cells held in a sample case having a holding unit, which holds a sample including the cells, using the electrode pairs and a reaction of the cells thereto was observed, and have proposed the following configurations of the present invention.

That is, in order to achieve the above-mentioned object, according to an aspect of the present invention, there is provided a cell observation device for observing cell held by a sample case including a holding unit holding a sample including the cell, the cell observation device including: a mounting unit for holding the sample case thereon; an electrical stimulation unit including an electrode pair having a first electrode and a second electrode; and a position control unit for controlling a position of the electrical stimulation unit in a state in which the first electrode is disposed closer to the center of the holding unit than the second electrode when the electrode pair is disposed in the holding unit of the sample case, wherein a tip of the first electrode extends more than a tip of the second electrode.

Alternatively, according to another aspect of the present invention, there is provided an electrical stimulation device for being inserted into a sample case having a holding unit holding a sample including a cell and applying electrical stimulation to the cells, the electrical stimulation device including an electrode pair including a first electrode and a second electrode, wherein a tip of the first electrode extends more than a tip of the second electrode, and the first electrode is disposed closer to the center of the holding unit than the second electrode when the electrode pair is disposed in the holding unit of the sample case.

According to the cell observation device or the electrical stimulation device, by disposing the electrode pair including the first electrode and the second electrode in the holding unit formed in the sample case, it is possible to apply electrical stimulation to a sample including a cell using the electrode pair. Here, the tip of the first electrode disposed close to the center of the holding unit extends more than the tip of the second electrode disposed close to the circumference of the holding unit. Accordingly, even when the holding unit has a concave bottom, it is possible to cause the tip of the first electrode to easily approach the sample including a cell which is held on the bottom. As a result, it is possible to appropriately apply electrical stimulation to the sample from the electrode pair using only a simple position control mechanism and to obtain an appropriate evaluation result of the sample.

According to still another aspect of the present invention, there is provided a cell observation device for observing a cell held by a sample case including a holding unit holding a sample including the cell, the cell observation device including: a mounting unit for holding the sample case thereon; an electrical stimulation unit including an electrode pair having a first electrode and a second electrode; a position control unit for controlling a position of the electrical stimulation unit such that the electrode pair is disposed in the holding unit of the sample case; and a position adjusting unit for adjusting a relative position of a tip of the first electrode to a tip of the second electrode.

Alternatively, according to still another aspect of the present invention, there is provided an electrical stimulation device for being inserted into a sample case having a holding unit holding a sample including a cell and applying electrical stimulation to the cells, the electrical stimulation device including: an electrode pair including a first electrode and a second electrode; and a position adjusting unit for adjusting a relative position of a tip of the first electrode to a tip of the second electrode.

Alternatively, according to still another aspect of the present invention, there is provided a cell observation method for observing a cell held by a sample case having a holding unit holding a sample including the cell, using an electrode pair including a first electrode and a second electrode, the cell observation method including: a step of adjusting a relative position of a tip of the first electrode to a tip of the second electrode; and a step of applying electrical stimulation to the sample using the electrode pair.

According to the cell observation device, the electrical stimulation device, or the cell observation method, by disposing the electrode pair including the first electrode and the second electrode in the holding unit formed in the sample case, it is possible to apply electrical stimulation to a sample including a cell using the electrode pair. Here, the relative position of the tip of the first electrode to the tip of the second electrode can be adjusted. Accordingly, even when the holding unit has a concave bottom, it is possible to cause the tip of the first electrode to easily approach the sample including a cell which is held on the bottom. As a result, it is possible to appropriately apply electrical stimulation to the sample from the electrode pair when the electrode pair is disposed in the holding unit and to obtain an appropriate evaluation result of the sample.

Advantageous Effects of Invention

According to the present invention, it is possible to appropriately apply electrical stimulation to a cell disposed in a concave well.

DESCRIPTION OF EMBODIMENTS

Figure 1:
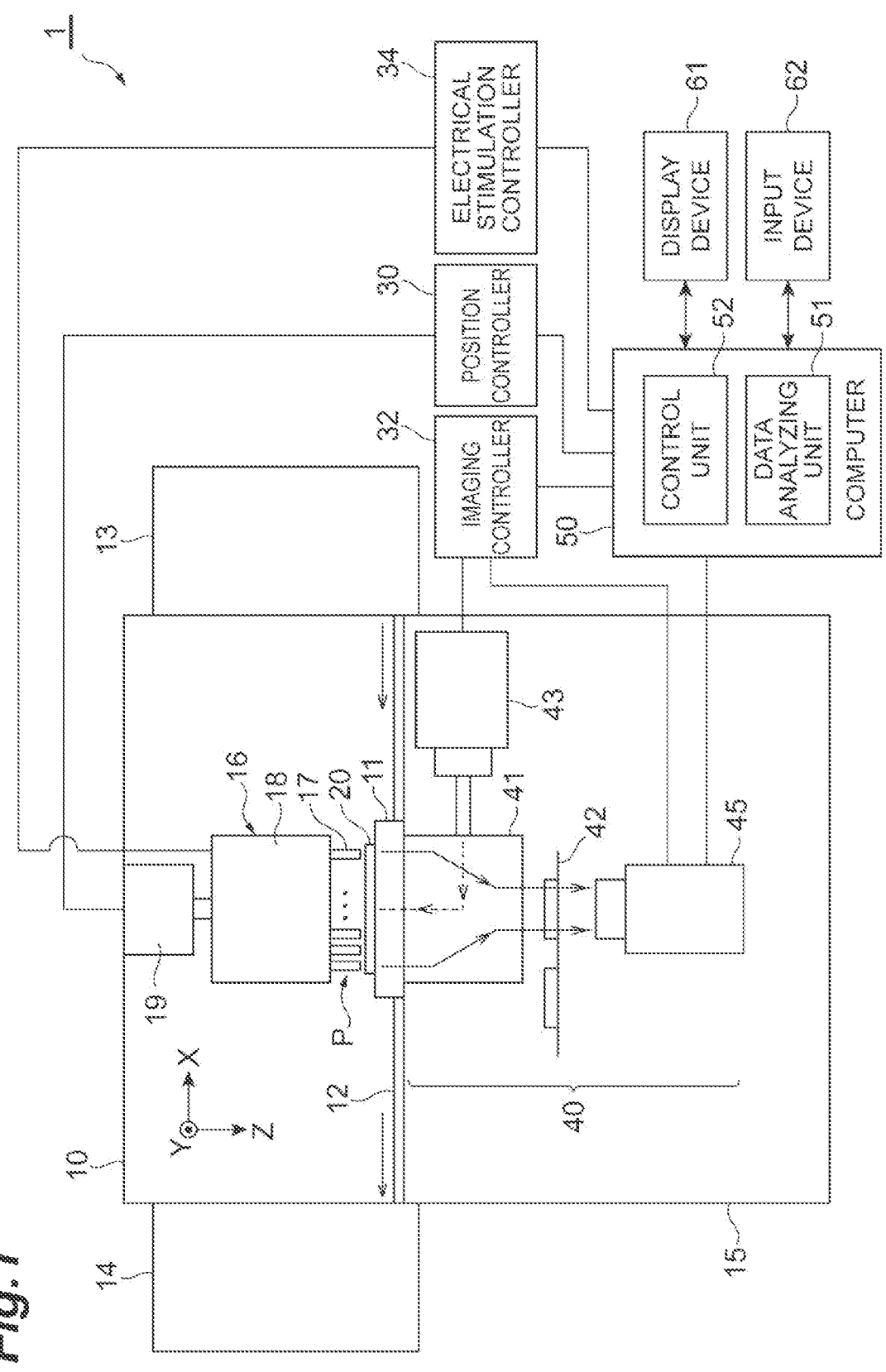
FIG. 1 is a diagram illustrating a schematic configuration of a cell observation device 1 according to a first embodiment of the present invention.

Hereinafter, a cell observation device, an electrical stimulation device, and a cell observation method according to embodiments of the present invention will be described in detail with reference to the accompanying drawings. In the description of the drawings, the same elements will be referenced by the same reference signs and description thereof will not be repeated. It should be noted that each of the drawings was prepared for the purpose of description and made with special emphasis on objects of description. For this reason, dimensional ratios of members in the drawings do not always agree with actual ones.

First Embodiment

Figure 2:
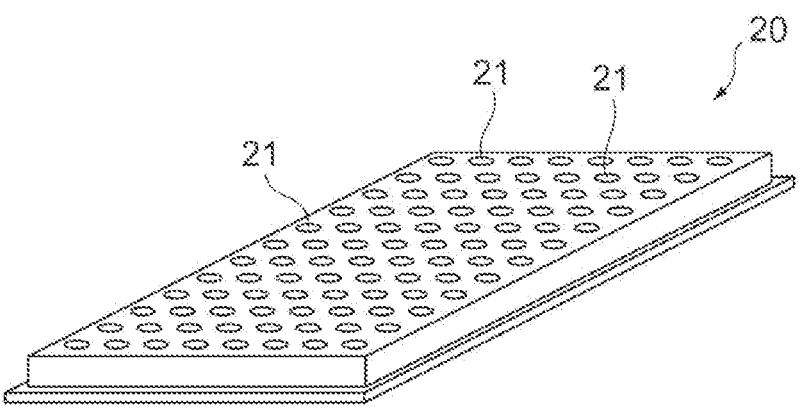
FIG. 2 is a perspective view illustrating a configuration of a microplate 20 illustrated in FIG. 1.
Figure 3:
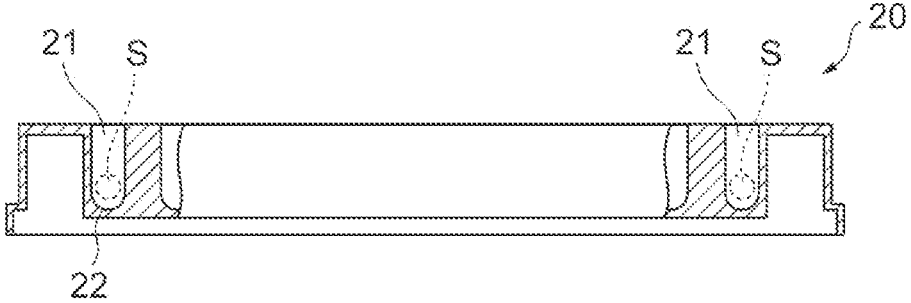
FIG. 3 is a side cross-sectional view illustrating a cross-sectional structure of the microplate 20 illustrated in FIG. 1.
Figure 4:
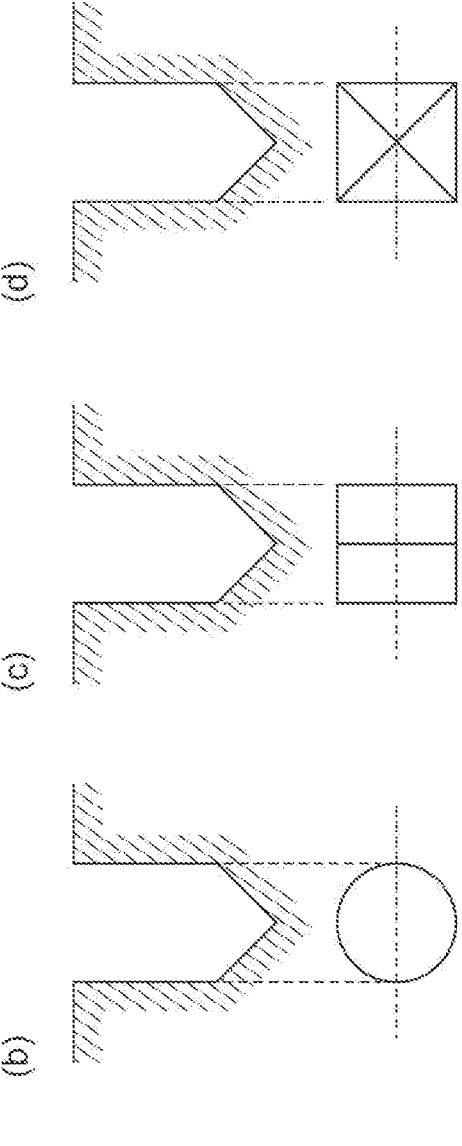
FIG. 4 is a diagram illustrating variations of a shape of a well which is formed in the microplate 20 illustrated in FIG. 1.

FIG. 1 is a diagram illustrating a schematic configuration of a cell observation device 1 according to a first embodiment of the present invention. FIG. 2 is a perspective view illustrating an example of a configuration of a microplate 20. FIG. 3 is a side cross-sectional view illustrating a cross-sectional structure of the microplate 20 illustrated in FIG. 2. FIG. 4 is a diagram illustrating variations of a shape of a well which is formed in the microplate 20. The cell observation device 1 according to this embodiment is a device for measuring fluorescence from a sample S, which is disposed at a measurement position P in a state in which the sample is held by the microplate 20, using the microplate 20 as a sample case.

The sample S includes predetermined cells. Examples of the predetermined cells include myocardial cells, muscle cells, which are differentiated from stem cells such as iPS (induced Pluripotent Stem) cells or ES (Embryonic Stem) cells, neurons, skin cells, photoreceptor cells, reproductive cells, and lever cells. The predetermined cells may be cells dyed with a membrane potential sensitive pigment, a calcium sensitive pigment, or a sodium ion sensitive pigment. The cell observation device, the electrical stimulation device, and the cell observation method according to this embodiment can be generally applied to optical measurement of measuring light such as phosphorescence and luminescence emitted from a sample as well as fluorescence measurement. The configuration of the cell observation device 1 will be described below.

The cell observation device 1 illustrated in FIG. 1 includes a data acquiring device 10, a position controller (position control unit) 30, an imaging controller 32, an electrical stimulation controller 34, and a computer 50 such as a PC. The data acquiring device 10 includes a dark box 15 that accommodates a microplate 20 holding cells to be subjected to fluorescence observation therein and a moving image acquiring unit 40 that is disposed in the dark box 15 and is used to measure fluorescence from a sample S disposed at the measurement position P. The position controller 30, the imaging controller 32, and the electrical stimulation controller 34 may be disposed in the data acquiring device 10.

The microplate 20 which is used as a sample case in this embodiment is a plate-shaped member in which a plurality of wells (holding units) 21 are arranged in a two-dimensional array and has a configuration in which each of the plurality of wells 21 can hold a sample S, as illustrated in FIGS. 2 and 3. In the configuration example illustrated in FIG. 2, 8×12=96 circular wells 21 are arranged in a two-dimensional array as the plurality of wells 21. The number of wells 21 arranged may be any number such as 6, 24, and 364. Examples of an opening shape of each well 21 (a cross-sectional shape of each well 21) include a circular shape, an elliptical shape, and a rectangular shape. As illustrated in FIG. 3, the cross-sectional shape in the depth direction of the bottom of each well 21 is a U shape which is a concave shape. When the microplate having a concave cross-sectional shape is used, cells can be easily settled on the bottom of each well 21 in culturing cells in the well 21 and thus there is a merit that the cells can be localized in the well and the cells can be stereoscopically formed in the well 21.

The bottom face 22 of the microplate 20 is formed of a material (for example, glass, quartz glass, polyethylene, polypropylene, or polystyrene) which can transmit fluorescence-measuring excitation light applied to the sample S and fluorescent light emitted from the sample S. In general, in the cell observation device 1, the bottom face 22 of the microplate 20 only has to be formed of a material which can transmit light emitted from the sample S to be measured.

In the dark box 15, the microplate 20 is placed on a microplate holder (mounting unit) 11 having an opening for fluorescence observation. A microplate carrying mechanism 12 that carries the microplate 20 and the microplate holder 11 in a predetermined direction (a direction from right to left in FIG. 1) in the dark box 15 is installed in the dark box 15.

On one side of the dark box 15 which is an inlet side in the carrying direction of the microplate 20 in the carrying mechanism 12, an inlet-side microplate stacker 13 on which a predetermined number of (for example, 25) microplates 20 holding samples S before measurement are stacked is installed. On the other side of the dark box 15 which is an outlet side in the carrying direction of the microplate 20, an outlet-side microplate stacker 14 on which the microplate 20 after measurement is stacked is installed.

In this configuration, the microplate 20 carried in the dark box 15 from the inlet-side microplate stacker 13 is held by the microplate holder 11 and is carried by the carrying mechanism 12. The microplate 20 is temporarily stopped at the measurement position P, and necessary optical measurement is performed on the sample S held by the microplate 20 in this state. After the measurement is completed, the microplate 20 is carried again by the carrying mechanism 12 and is carried out to the outlet-side microplate stacker 14. In FIG. 1, the configurations for carrying in, carrying, and carrying out the microplate 20 in the carrying mechanism 12 and the stackers 13 and 14 are not specifically illustrated.

Above the measurement position P at which the microplate 20 and the sample S are disposed at the time of optical measurement, an electrical stimulation unit (electrical stimulation device) 16 that is inserted into the well 21 of the microplate 20 and applies an electric field (electrical stimulation) to the sample S is installed. Below the measurement position P, a moving image acquiring unit 40 that is used to detect fluorescence emitted from the sample S accommodated in the well 21 via the bottom face 22 of the microplate 20 is installed.

The moving image acquiring unit 40 is moving image acquiring means for detecting a two-dimensional optical image representing a two-dimensional optical intensity distribution of the microplate 20 including light emitted from the sample S held in the well 21 of the microplate 20 and acquiring moving image data of the two-dimensional optical image. The detected two-dimensional optical image may be a optical intensity distribution including light emitted from the sample S held in at least one well 21. The moving image acquiring unit 40 includes an imaging device 45, a light-guiding optical system 41, an optical filer unit 42, and an excitation light source 43. The imaging device 45 has a two-dimensional pixel structure in which a plurality of pixels are two-dimensionally arranged and detects a fluorescent image which is a two-dimensional detected optical image based on fluorescence emitted from the sample S. For example, a camera equipped with an area image sensor such as a CCD image sensor or a CMOS image sensor with high sensitivity can be used as the imaging device 45. If necessary, the moving image acquiring unit 40 may be configured by disposing an image intensifier such as a micro channel plate (MCP), a relay lens, and the like in the front of the camera. The moving image acquiring unit 40 may acquire a still image and has a function of an image acquiring unit that acquires a moving image and/or a still image.

The light-guiding optical system 41 is installed between the measurement position P at which the microplate 20 is disposed and the imaging device 45. The light-guiding optical system 41 is an optical system that guides a two-dimensional optical image, which is obtained when the microplate 20 holding the samples S of the plurality of wells 21 is viewed from the bottom face 22, to the imaging device 45. The light-guiding optical system 41 can be specifically appropriately configured using optical elements that can implement necessary functions (for example, a focusing function and a optical image reducing function) depending on the configurations of the microplate 20 and the imaging device 45. An example of such an optical element is a taper fiber (see Japanese Unexamined Patent Publication No. 2001-188044). The light-guiding optical system 41 may have a configuration using a light irradiation device with a light guide member having concavities and convexities (see Japanese Unexamined Patent Publication No. 2010-230397 and Japanese Unexamined Patent Publication No. 2010-230396).

In FIG. 1, the optical filer unit 42 that can dispose, switch, and the like an optical filter to a light-guiding optical path if necessary is installed between the light-guiding optical system 41 and the imaging device 45. Here, the optical filer unit 42 may not be installed if not necessary.

The excitation light source 43 is excitation light supply means for supplying fluorescence-measuring excitation light to the sample S. The excitation light source 43 can be specifically appropriately configured depending on the type of the sample S to be subjected to fluorescence measurement, the wavelength of excitation light to be applied to the sample S, and the like. For example, the excitation light source can be configured using an illumination light source that supplies light and an optical filter unit that selects and switches the wavelength of excitation light. When supply of excitation light is not necessary depending on the type of optical measurement which is performed on the sample S, the excitation light source 43 may not be installed.

In this embodiment, the light-guiding optical system 41 includes an optical system that can guide a two-dimensional optical image from the microplate 20 and the sample S to the imaging device 45 and guide excitation light from the excitation light source 43 to the sample S. Such an optical system can be configured, for example, using a dichroic mirror that transmits fluorescence from the microplate 20 and reflects excitation light from the excitation light source 43 or the like. In FIG. 1, optical paths of fluorescence and excitation light in the light-guiding optical system 41 are schematically indicated by a solid line and a dotted line, respectively.

The microplate 20 which is used in the cell observation device 1 can employ various shapes of a well 21. Parts (a)-(d) in FIG. 4 illustrate variations of the concave shape of a well 21 and each of parts illustrate a cross-sectional view taken along the depth direction of the well 21 in the upper part and a plan view when viewed from the depth direction of the well in the lower part. As illustrated in the drawing, a well having a bottom of a U-shaped cross-sectional shape, a well having a bottom of a V-shaped cross-sectional shape, a well having a bottom of a conical shape, or a well having a bottom of a pyramidal shape can be used as the well 21. Even when the wells 21 having such shapes are used, there is a merit that a cell can be localized in the well and a cell can be stereoscopically formed in the well 21.

The configuration of the electrical stimulation unit 16 will be described below in detail.

The electrical stimulation unit 16 has a structure in which a plurality of electrode pairs 17 extending vertically to the microplate 20 are fixed to a base 18 so as to be two-dimensionally arranged. Specifically, the electrode pairs 17 are arranged in a two-dimensional shape corresponding to the two-dimensional array of the plurality of wells 21 of the microplate 20 so as to extend to face the wells 21 of the microplate 20.

Figure 5:
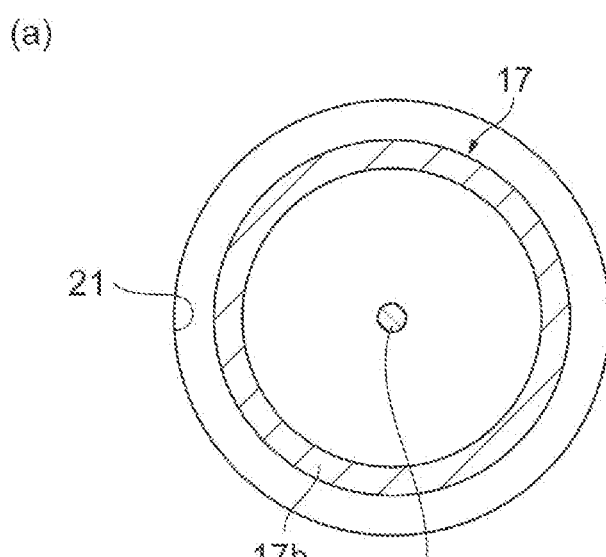
FIG. 5 is a diagram illustrating a structure of an electrode pair 17 in a state in which an electrical stimulation unit 16 illustrated in FIG. 1 is inserted into a well.
Figure 5:
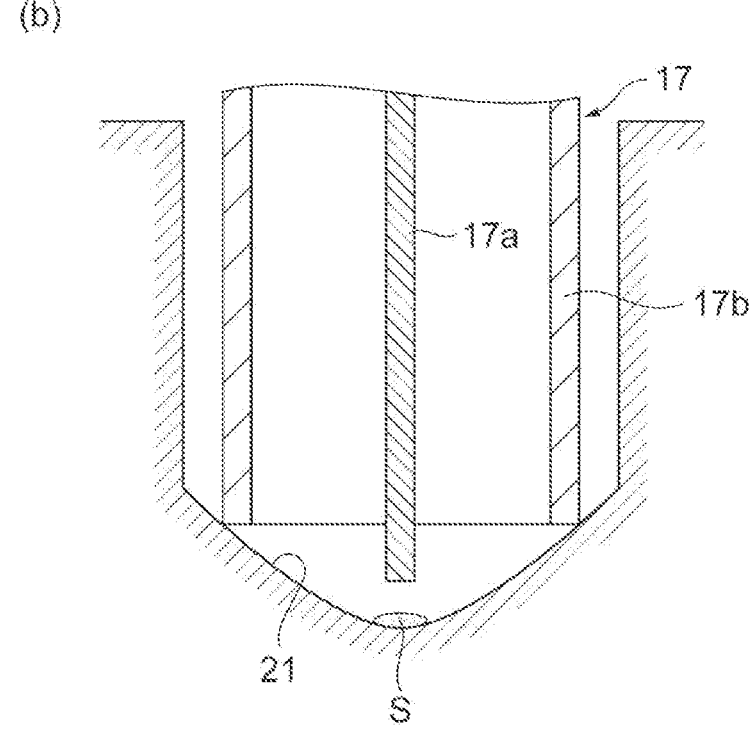

FIG. 5 illustrates a structure of an electrode pair 17 in a state in which the electrical stimulation unit 16 is inserted into a well of the microplate 20, where a portion (a) in FIG. 5 is a cross-sectional view taken along the opening of the well 21 and a portion (b) in FIG. 5 is a cross-sectional view taken along the depth direction of the well 21. As illustrated in the drawing, the electrode pair 17 includes a first electrode 17a having a rod shape (for example, a columnar shape) extending in the depth direction of the well 21 and a second electrode 17b having a cylindrical shape in which the tip is opened and the first electrode 17a is located in the axis therein. The outer diameter of the second electrode 17b is set to be smaller than the inner diameter of the well 21. The electrode pair 17 has a structure in which the tip of the first electrode 17a on the bottom side of the well 21 extends more than the tip of the second electrode 17b on the bottom side of the well 21. The electrode pair 17 having this shape is positioned by bringing the second electrode 17b having a cylindrical shape into contact with the bottom face 22 of the well 21 when the electrode pair is inserted into the well 21. At this time, the second electrode 17b can be easily fitted to the well 21 having a U shape or a conical shape and the electrode pair 17 can be easily positioned. Since the first electrode 17a extends more than the second electrode 17b, it is possible to reduce a distance between the sample S located on the bottom face 22 and the tip of the first electrode 17a and to efficiently apply electrical stimulation to the sample S.

Figure 6:
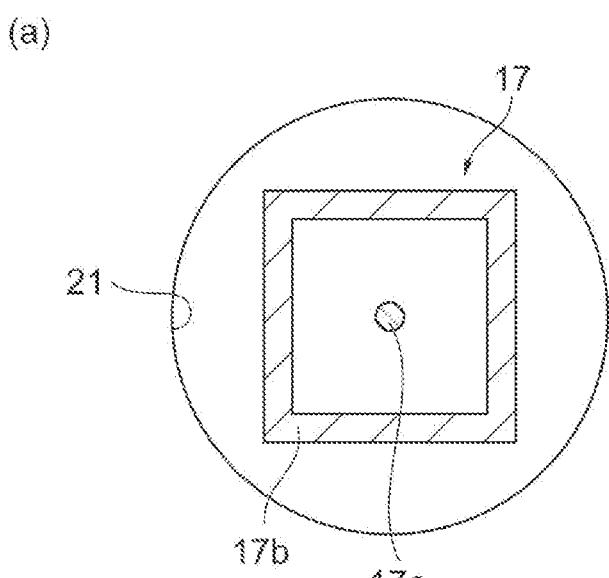
FIG. 6 is a diagram illustrating another structure of the electrode pair 17 in a state in which the electrical stimulation unit 16 illustrated in FIG. 1 is inserted into a well.
Figure 6:
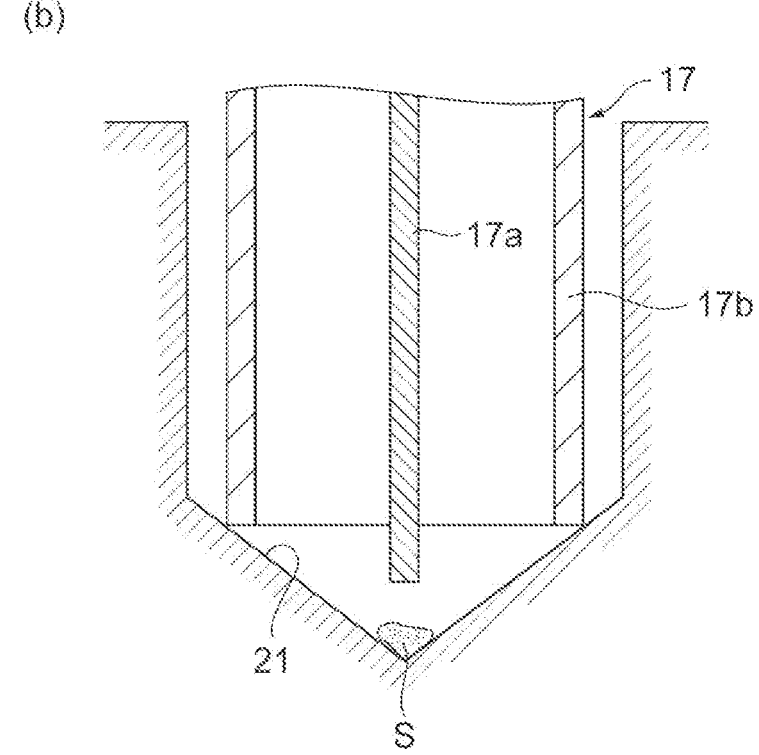

FIG. 6 illustrates another structure of an electrode pair 17 in a state in which the electrical stimulation unit 16 is inserted into a well 21 of the microplate 20, where a portion (a) in FIG. 6 is a cross-sectional view taken along the opening of the well 21 and a portion (b) in FIG. 6 is a cross-sectional view taken along the depth direction of the well 21. As illustrated in the drawing, the electrode pair 17 includes a first electrode 17a having a rod shape (for example, a columnar shape) extending in the depth direction of the well 21 and a second electrode 17b having a rectangular tubular shape in which the tip is opened and the first electrode 17a is located in the axis therein. The electrode pair 17 has a structure in which the tip of the first electrode 17a on the bottom side of the well 21 extends more than the tip of the second electrode 17b on the bottom side of the well 21. The second electrode 17b can be easily fitted to the well 21 having a pyramidal shape and the electrode pair 17 can be easily positioned with respect to the well 21. Since the first electrode 17a extends more than the second electrode 17b, it is possible to reduce a distance between the sample S located on the bottom face 22 and the tip of the first electrode 17a and to efficiently apply electrical stimulation to the sample S.

Figure 7:
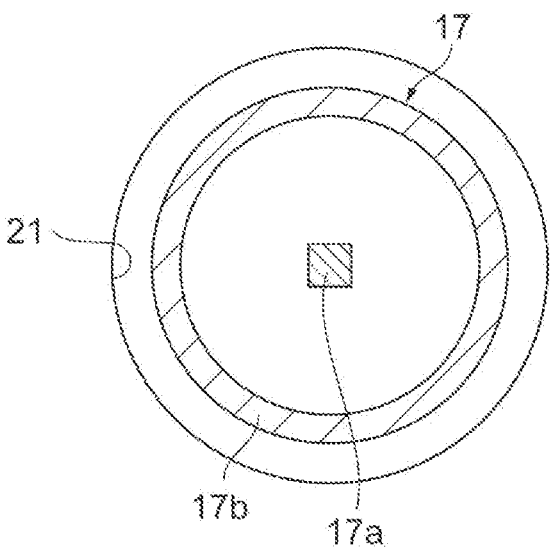
FIG. 7 is a diagram illustrating another structure of the electrode pair 17 in a state in which the electrical stimulation unit 16 illustrated in FIG. 1 is inserted into a well.
Figure 8:
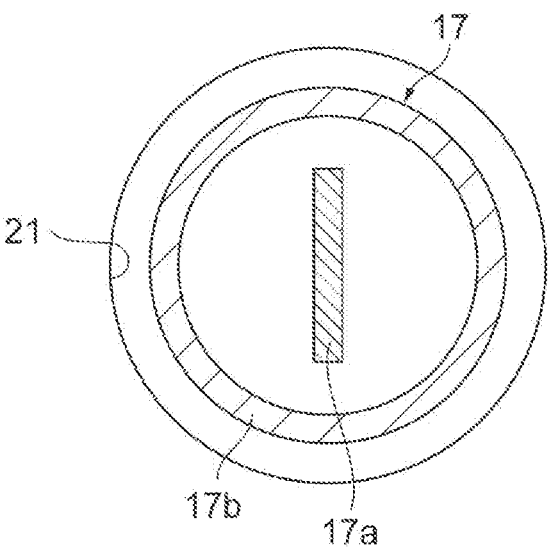
FIG. 8 is a diagram illustrating another structure of the electrode pair 17 in a state in which the electrical stimulation unit 16 illustrated in FIG. 1 is inserted into a well.
Figure 9:
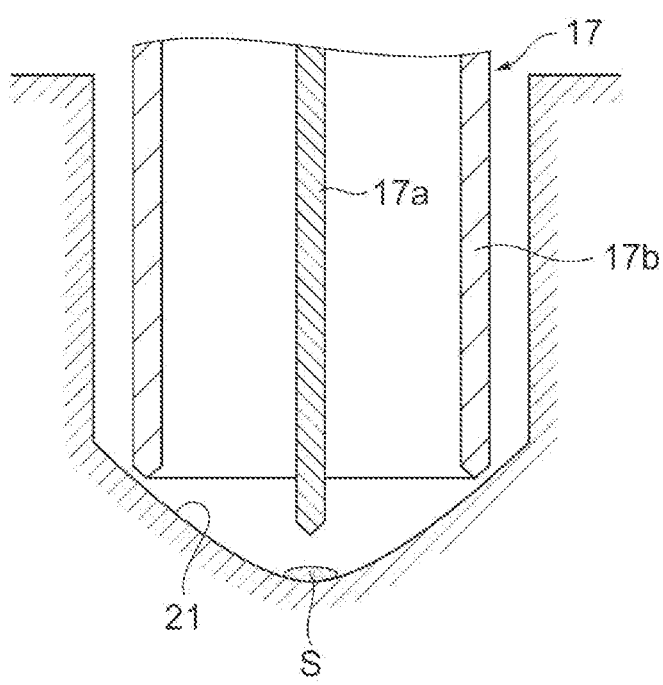
FIG. 9 is a diagram illustrating another structure of the electrode pair 17 in a state in which the electrical stimulation unit 16 illustrated in FIG. 1 is inserted into a well.

The first electrode 17a of the electrode pair 17 may have various shapes other than the columnar shape. FIGS. 7 and 8 are cross-sectional views of the electrode pair 17 taken along the opening of the well 21 in a state in which the electrical stimulation unit 16 is inserted into the well 21. As illustrated in the drawings, the first electrode 17a may have a prism shape or a plate shape. One or both of the tips of the first and second electrodes 17a and 17b of the electrode pair 17 on the bottom side of the well 21 may have a sharpened or rounded convex shape. FIG. 9 is a cross-sectional view of the electrode pair 17 having a convex shape taken along the depth direction of the well 21. According to the first electrode 17a having this shape, it is possible to more efficiently apply electrical stimulation to the sample S in the vicinity of the first electrode 17a. According to the second electrode 17b having this shape, it is possible to easily fit the electrode pair 17 to a well 21 having a U shape or a well 21 having a pyramidal shape.

Figure 10:
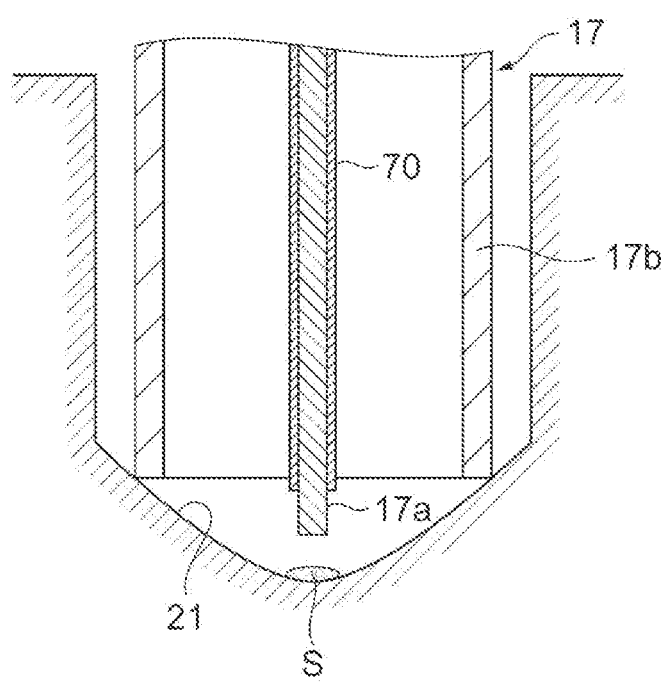
FIG. 10 is a diagram illustrating another structure of the electrode pair 17 in a state in which the electrical stimulation unit 16 illustrated in FIG. 1 is inserted into a well.

The first electrode 17a of the electrode pair 17 may be coated with an insulator except for the tip which is used to apply electrical stimulation to the sample S. FIG. 10 is a cross-sectional view of the electrode pair 17 coated with an insulator taken along the depth direction of the well 21. As illustrated in the drawing, the first electrode 17a except for the tip on the bottom side of the well 21 is coated with an insulator 70. According to the first electrode 17a having this configuration, it is possible to more efficiently apply electrical stimulation to the sample S. The insulator 70 can be formed in the first electrode 17a by coating the first electrode with an insulating material or covering the first electrode with an insulating tube.

Here, the electrode pair 17 is not limited to the configuration in which each of the first electrode 17a and the second electrode 17b is formed of a single member, but one or both may be formed of plural members.

Referring to FIG. 1 again, the electrical stimulation unit 16 is provided with a moving mechanism 19 that supports the electrode pairs 17 via the base 18. The moving mechanism 19 is a driving mechanism that moves the electrode pairs 17 to approach or retract from the microplate 20 (in the Z direction in FIG. 1), drives the electrode pairs 17 to be disposed in the corresponding wells 21 at the time of observation of the samples S, and drives the electrode pairs 17 to depart from the wells 21 at the time of end of observation of the samples S. Accordingly, each electrode pair 17 can be disposed in the corresponding well 21 in a state in which the first electrode 17a is disposed closer to the center of the well 21 than the second electrode 17b. The moving mechanism 19 may move the electrode pairs 17 in a direction along the bottom face 22 of the microplate 20 (a direction parallel to the plan including the X axis and the Y axis in FIG. 1). In this case, the moving mechanism 19 can improve accuracy of position adjustment of disposing the first electrode 17a closer to the center of the well 21 than the second electrode 17b. A configuration for moving the microplate holder 11 on which the microplate 20 is mounted in a Z direction in FIG. 1 or a direction parallel to a plane including the X axis and the Y axis in FIG. 1 may be employed instead of the moving mechanism 19.

The position controller (position control unit) 30, the imaging controller 32, and the electrical stimulation controller 34 are connected to the data acquiring device 10 having the above-mentioned configuration. The position controller 30 is electrically connected to the moving mechanism 19 and controls the moving mechanism 19 to dispose the electrode pairs 17 in the wells 21 of the microplate 20 when the optical measurement of the samples S is started. Specifically, the position controller 30 controls the position of each electrode pair 17 such that the electrode pair 17 is inserted into and removed from the well 21 in a state in which the first electrode 17a is disposed closer to the center of the well 21 than the second electrode 17b when the electrode pair 17 is disposed in the well 21, as illustrated in FIGS. 5 to 10. More specifically, the position controller 30 controls the tip of the first electrode 17a so as to be located close to the center of the bottom face 22 of the well 21 by inserting (moving) the electrode pair 17 into the well 21 such that the tip of the second electrode come in contact with the outside of the center of the bottom face 22 of the well 21. The electrical stimulation controller 34 is electrically connected to the electrical stimulation unit 16, supplies an electrical signal to the first electrode 17a and the second electrode 17b of the electrode pair 17 to apply electrical stimulation such as a voltage or a current to the sample S. The imaging controller 32 controls irradiation of excitation light from the excitation light source 43 and capturing a two-dimensional fluorescence image of the microplate 20 in the imaging device 45.

The position controller 30, the imaging controller 32, and the electrical stimulation controller 34 are connected to the computer 50. The computer 50 includes a data analyzing unit 51 that acquires moving image data including a detected optical image acquired by the moving image acquiring unit 40 and performs an analysis process on the moving image data. The computer 50 includes a control unit 52 that controls operations of the units of the data acquiring device 10 via the position controller 30, the imaging controller 32, and the electrical stimulation controller 34 and controls fluorescence measurement of the sample S in the cell observation device 1 (details of which will be described later). In FIG. 1, the computer 50 is connected to a display device 61 that displays a measurement result and the like and an input device 62 that is used to input data and to input an instruction required for the fluorescence measurement.

Figure 11:
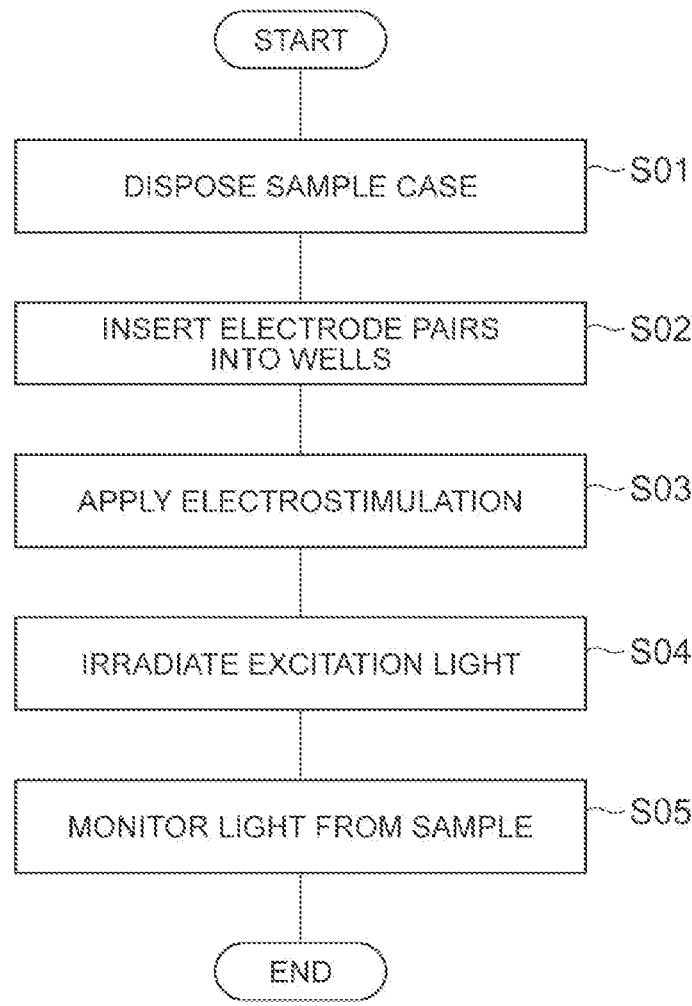
FIG. 11 is a flowchart illustrating an operation of the cell observation device 1 illustrated in FIG. 1 at the time of optical measurement of a sample S.

The operation of the cell observation device 1 at the time of optical measurement of a sample S and the cell observation method according to this embodiment will be described below with reference to FIG. 11. FIG. 11 is a flowchart illustrating the operation of the cell observation device 1 at the time of optical measurement of a sample S. First, when an instruction to start optical measurement of cells is input via the input device 62, the microplate 20 holding a sample S to be measured in the microplate stacker 13 is carried to the measurement position P in the dark box 15 by the microplate carrying mechanism 12 in a state in which the microplate is placed on the microplate holder 11 (step S01). Then, by causing the computer 50 to control the position of the electrical stimulation unit 16 using the moving mechanism 19, the tips of a plurality of electrode pairs 17 are inserted into the corresponding wells 21 of the microplate 20 (step S02). At this time, the computer 50 controls the positions of the electrode pairs 17 such that the tip of the second electrode 17b of each electrode pair 17 comes in contact with the outside of the center of the bottom face 22 of the microplate 20. Accordingly, the first electrode 17a is disposed in a state in which the tip thereof is separated by a predetermined distance from the center of the bottom face 22 of the well 21.

Thereafter, by causing the computer 50 to control the electrical stimulation controller 34, an electrical signal is supplied to the electrode pairs 17 and electrical stimulation is applied to the samples S in the wells 21 of the microplate 20 (step S03). The irradiation of electrical stimulation is repeatedly performed with a predetermined cycle (for example, 1 to 10 Hz). In the state in which the application of electrical stimulation is started, application of excitation light from the excitation light source 43 is started by causing the computer 50 to control the imaging controller 32 (step S04). Then, a two-dimensional optical image of the microplate 20 including fluorescence emitted from the sample S held in the well 21 is detected by the moving image acquiring unit 40, and moving image data representing the two-dimensional optical image is acquired by the computer 50. The frame rate of the moving image acquiring unit 40 is set to be higher than the frequency of the electrical signal. By causing the computer 50 to perform optical intensity analysis in the analysis area set as an area of the microplate 20 on the microplate holder 11 facing the electrode pair 17 on the two-dimensional optical image included in the acquired moving image data, analysis information (monitoring result) of the sample S is acquired and is output to the display device 61 (step S05).

For example, when the sample S includes myocardial cells exposed to a reagent, the analysis information is obtained by monitoring the fluorescence intensity from the myocardial cells dyed with a calcium ion sensitive pigment in time series. At this time, since a strength or cycle of a heartbeat can be aligned by applying electrical stimulation to the myocardial cells, it is possible to quantitatively evaluate the reagent. Accordingly, it is possible to evaluate a side effect of the reagent on the myocardial cells. When the cells in the sample S are dyed with a membrane potential sensitive fluorescent pigment and electrical stimulation is applied thereto, a variation in membrane potential with opening and closing of an ion channel of the cells is observed as a variation in fluorescence intensity. When the sample S include cells dyed with a membrane potential sensitive pigment or a sodium ion sensitive pigment, the membrane potential may be controlled by applying electrical stimulation to the sample S. As a technique of analyzing optical intensity in the analysis area, a technique of calculating the amplitude, the changing rate, the peak cycle, the number of peaks, the peak time, the rising time, the falling time, and the peak fluctuation width, and the like of the change of the pixel values in the analysis area as evaluation values can be considered.

According to the above-mentioned cell observation device 1 and the cell observation method using the cell observation device 1, by disposing the electrode pair 17 including the first electrode 17a and the second electrode 17b in the well 21 installed in the microplate 20, it is possible to apply electrical stimulation to a sample S including cells using the electrode pair 17. Here, since the tip of the first electrode 17a disposed close to the center of the well 21 extends more than the tip of the second electrode 17b disposed close to the circumference of the well 21, it is possible to cause the tip of the first electrode 17a to approach the sample S including cells held on the bottom of the well even when the well 21 has a concave bottom. Accordingly, it is possible to apply electrical stimulation to the sample S from the electrode pair 17 by only using a simple position control mechanism and to obtain an appropriate evaluation result for the sample S.

With the above-mentioned structure of the electrode pair 17, it is possible to easily fit the shape of the electrode pair 17 to the concave internal shape of the well 21 and to reduce the distance between the sample S held on the bottom of the well 21 and the first electrode 17a when the electrode pair 17 is disposed in the well 21 of the microplate 20. As a result, it is possible to efficiently apply electrical stimulation to the sample S. When the first electrode 17a as a pillar shape, it is possible to easily reduce the distance between the sample S held on the bottom of the well 21 and the first electrode 17a. As a result, it is possible to efficiently apply electrical stimulation to the sample S.

Second Embodiment

Figure 12:
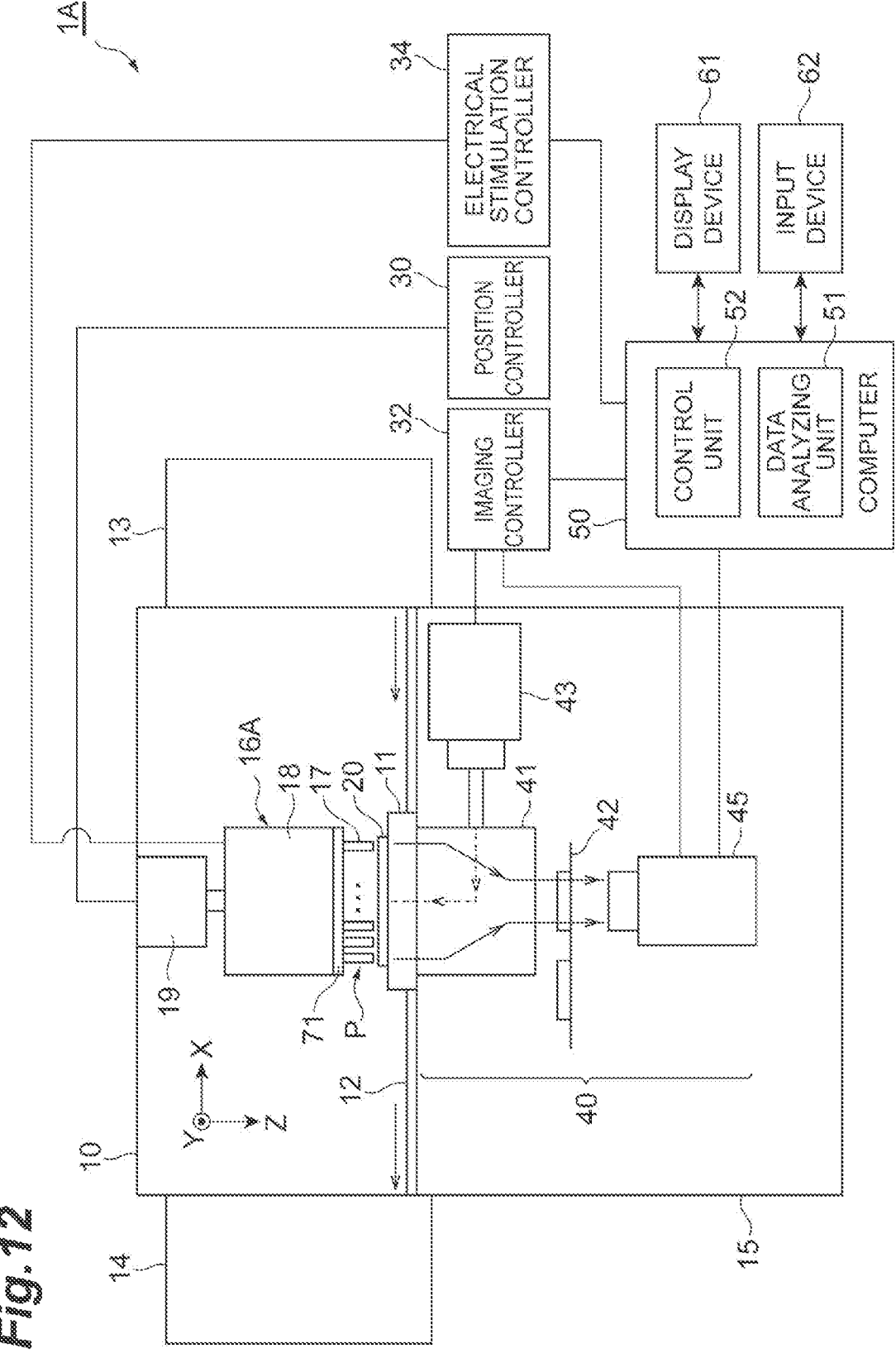
FIG. 12 is a diagram illustrating a schematic configuration of a cell observation device 1A according to a second embodiment of the present invention.

A second embodiment of the present invention will be described below. FIG. 12 is a diagram schematically illustrating a configuration of a cell observation device 1A according to the second embodiment of the present invention.

The cell observation device 1A illustrated in the drawing is different from the cell observation device 1 according to the first embodiment, in that an electrical stimulation unit 16A includes a position adjusting mechanism 71. The other configuration of the cell observation device 1A is the same as in the first embodiment. The position adjusting mechanism 71 is fixed to the base 18 of the electrical stimulation unit 16A and supports the electrode pairs 17 so as to independently move the first electrode 17a and the second electrode 17b.

Figure 13:
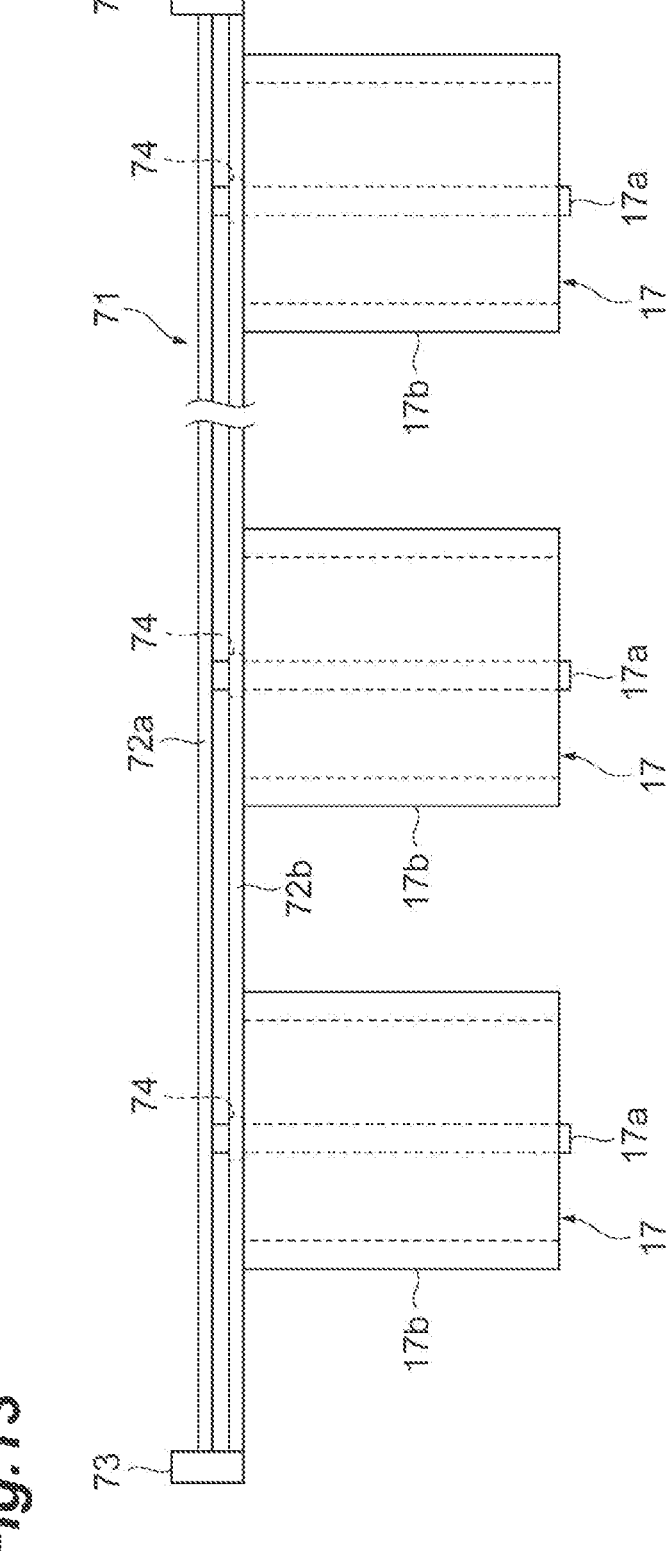
FIG. 13 is a side view illustrating a detailed configuration of a position adjusting mechanism 71 illustrated in FIG. 12.
Figure 14:
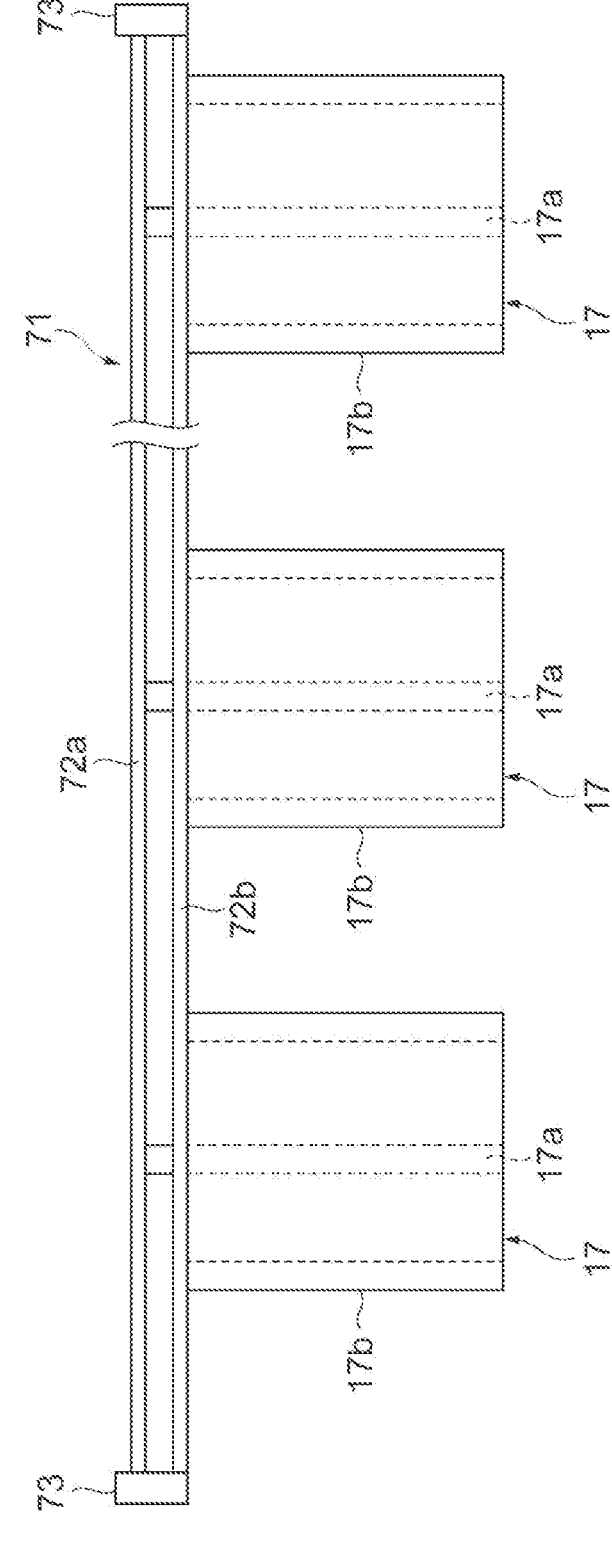
FIG. 14 is a side view illustrating a detailed configuration of the position adjusting mechanism 71 illustrated in FIG. 12.
Figure 15:
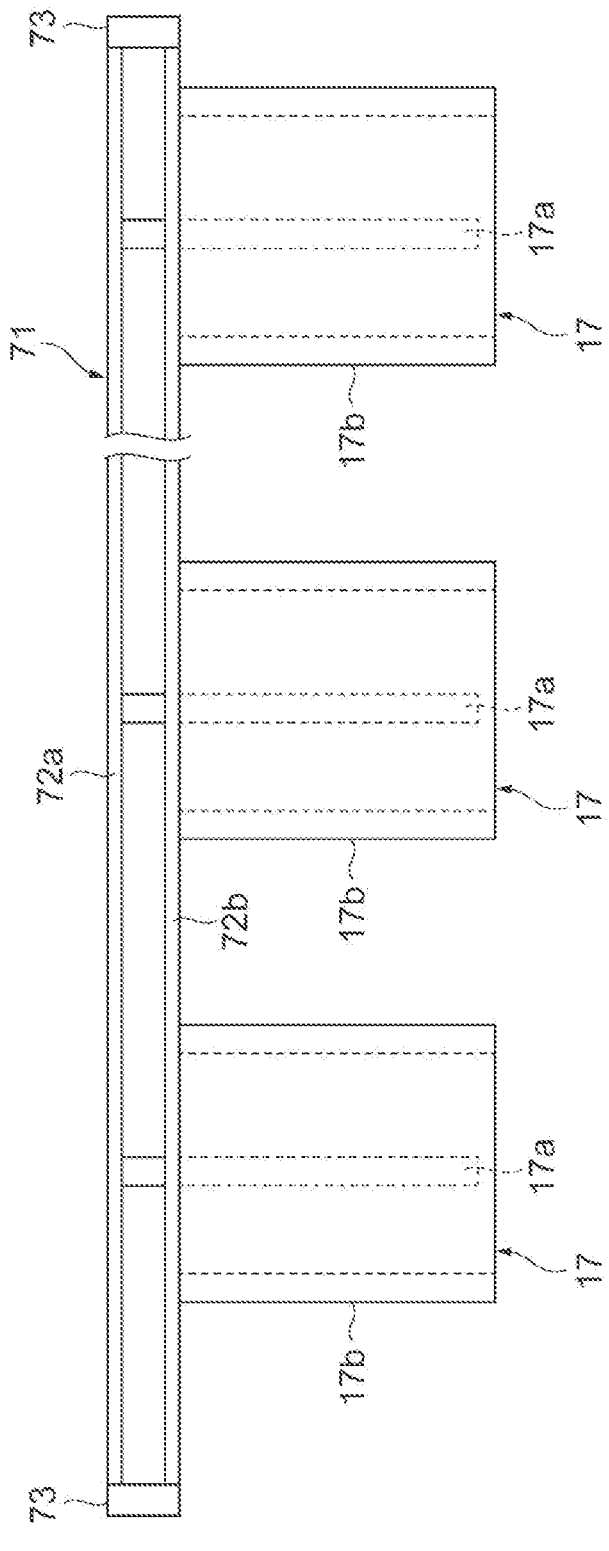
FIG. 15 is a side view illustrating a detailed configuration of the position adjusting mechanism 71 illustrated in FIG. 12.

FIGS. 13 to 15 illustrate a detailed configuration of the position adjusting mechanism 71. As illustrated in the drawings, the position adjusting mechanism 71 includes a longitudinal first support 72a that supports base ends of the first electrodes 17a of the plurality of electrode pairs 17 on the base 18 side, a longitudinal second support 72b that supports base ends of the second electrodes 17b of the plurality of electrode pairs 17 on the base 18 side, and an adjustment unit 73 that moves the first and second supports 72a and 72b so as to adjust the distance between the first and second supports 72a and 72b. The second support 72b is provided with through-holes 74 through which the first electrodes 17a pass.

According to the position adjusting mechanism 71 having the above-mentioned configuration, it is possible to independently move the first electrodes 17a of the plurality of electrode pairs 17 and the second electrodes 17b of the plurality of electrode pairs 17 in the direction parallel to the axis of the second electrodes 17b (the length direction of the first electrodes 17a). As a result, it is possible to simultaneously adjust the relative positions of the tip of the first electrode 17a to the tip of the second electrode 17b in the plurality of electrode pairs 17. Particularly, according to the configuration in which the plurality of first electrodes 17a and the plurality of second electrodes 17b are attached to the first and second supports 72a and 72b, respectively, it is possible to simultaneously and easily adjust the positions of the tips of the plurality of electrode pairs 17.

Specifically, as illustrated in FIG. 13, it is possible to adjust the tip positions such that the tip of the first electrode 17a extends more than the tip of the second electrode 17b. As illustrated in FIGS. 14 and 15, when each well 21 of the microplate 20 has a flat bottom, it may be possible to adjust the tip positions such that the tip of the first electrode 17a and the tip of the second electrode 17b have the same height from the base 18 and it may be possible to adjust the tip positions such that the tip of the second electrode 17b extends more than the tip of the first electrode 17a.

The position adjusting mechanism 71 may fix the position of the second support 72b and adjust the distance of the first support 72a from the base 18, or may fix the position of the first support 72a and adjust the distance of the second support 72b from the base 18, or may adjust the distances of the first and second supports 72a and 72b from the base 18. In any case, it is possible to adjust the relative position of the tip of the first electrode 17a and the tip of the second electrode 17b. The position adjusting mechanism 71 may be constituted by an electrical driving unit using a piezoelectric actuator or a stepping motor, may be constituted by a manual mechanism that can manually adjust a position, or may have a structure employing a screw structure. When the position adjusting mechanism 71 is constituted by the electrical driving unit, the adjustment unit 73 is electrically connected to the position controller 30 and the positions of the first and second supports 72a and 72b can be electronically controlled using a control signal from the position controller 30.

When the position adjusting mechanism 71 is configured to be electrically controllable, the position of the electrode pair 17 may be controlled as follows. First, shape information of the wells 21 (for example, information indicating that the bottom has a flat shape or a U shape or depth information of a U-shaped bottom) of the microplate 20 which is used for observation or information on the tip position (width or height information) of the first electrode 17a relative to the tip position of the second electrode 17b is input by the input device 62. Then, the relative position of the tip of the first electrode 17a to the tip of the second electrode 17b is determined and the gap between the first support 72a and the second support 72b is automatically adjusted to achieve the relative position, by the position controller 30. In this way, the position adjusting mechanism 71 can adjust the relative position of the tip of the first electrode 17a to the tip of the second electrode 17b.

Figure 16:
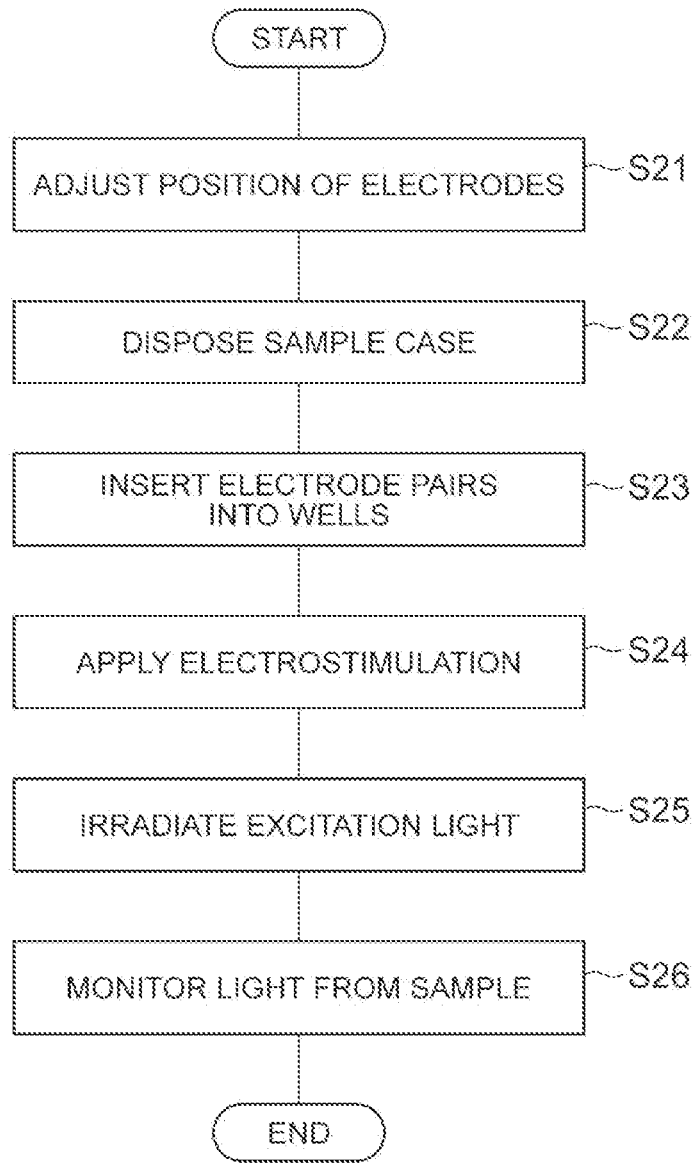
FIG. 16 is a flowchart illustrating an operation of the cell observation device 1A illustrated in FIG. 1 at the time of optical measurement of a sample S.

The operation of the cell observation device 1A at the time of optical measurement of a sample S and the cell observation method according to this embodiment will be described below in detail with reference to FIG. 16. FIG. 16 is a flowchart illustrating the operation of the cell observation device 1A at the time of optical measurement of a sample S.

First, when an instruction to start the optical measurement of cells and shape information of the wells 21 are input via the input device 62, the positional relationship between the tip of the first electrode 17a and the tip of the second electrode 17b in the plurality of electrode pairs 17 is automatically adjusted under the control of the position controller 30 (step S21). Thereafter, the microplate 20 holding a sample S to be measured in the microplate stacker 13 is carried to the measurement position P in the dark box 15 by the microplate carrying mechanism 12 in a state in which the microplate is placed on the microplate holder 11 (step S22). Then, by causing the computer 50 to control the position of the electrical stimulation unit 16 using the moving mechanism 19, the tips of the plurality of electrode pairs 17 are inserted into the corresponding wells 21 of the microplate 20 (step S23). At this time, the computer 50 controls the positions of the electrode pairs 17 such that the tip of the second electrode 17b of each electrode pair 17 comes in contact with the outside of the center of the bottom face 22 of the microplate 20. Accordingly, the first electrode 17a is disposed in a state in which the tip thereof is separated by a predetermined distance from the center of the bottom face 22 of the well 21.

Thereafter, by causing the computer 50 to control the electrical stimulation controller 34, an electrical signal is supplied to the electrode pairs 17 and electrical stimulation is applied to the samples S in the wells 21 of the microplate 20 (step S24). The application of electrical stimulation is repeatedly performed with a predetermined cycle (for example, 1 to 10 Hz). In the state in which the application of electrical stimulation is started, irradiation of excitation light from the excitation light source 43 is started by causing the computer 50 to control the imaging controller 32 (step S25). Then, a two-dimensional optical image of the microplate 20 including fluorescence emitted from the sample S held in the well 21 is detected by the moving image acquiring unit 40, and moving image data representing the two-dimensional optical image is acquired by the computer 50. The frame rate of the moving image acquiring unit 40 is set to be higher than the frequency of the electrical signal. By causing the computer 50 to perform optical intensity analysis in the analysis area set as an area of the microplate 20 on the microplate holder 11 facing the electrode pair 17 on the two-dimensional optical image included in the acquired moving image data, analysis information (monitoring result) of the sample S is acquired and is output to the display device 61 (step S26).

Here, the process of adjusting the position of the electrode pair 17 in step S21 may be performed when the electrode pair 17 is inserted into the well 21 in step S22. The process of step S21 may be performed after the process of inserting the electrode pair 17 into the well 21 in step S23 and before the process of starting application of electrical stimulation in step S24, or a cycle of evaluating a reaction of the sample S on the basis of a monitoring result of light from the sample in step S26, performing the process of adjusting the position of the electrode pair 17 in step S21, performing the process of applying electrical stimulation in step S24, performing the process of irradiating excitation light in step S25, and performing the process of monitoring light in step S26 may be carried out. This cycle may be repeated plural times. As a result, it is possible to adjust the intensity of electrical stimulation (a voltage value or a current value) to be applied depending on the reaction of the sample S.

According to the above-mentioned cell observation device 1A and the cell observation method using the cell observation device 1A, by disposing the electrode pair 17 including the first electrode 17a and the second electrode 17b in the well 21 installed in the microplate 20, it is possible to apply electrical stimulation to a sample S including cells using the electrode pair 17. Here, since the relative position of the tip of the first electrode 17a to the tip of the second electrode 17b can be adjusted, it is possible to cause the tip of the first electrode 17a to approach the sample S including cells held on the bottom of the well even when the well 21 has a concave bottom. Even when the well 21 has another shape such as a flat bottom, the tip of the first electrode 17a can be made to appropriately approach the sample S to correspond to the shape. Accordingly, it is possible to apply electrical stimulation to the sample S from the electrode pair 17 when the electrode pair 17 is disposed in the well 21, and to obtain an appropriate evaluation result for the sample S.

Figure 17:
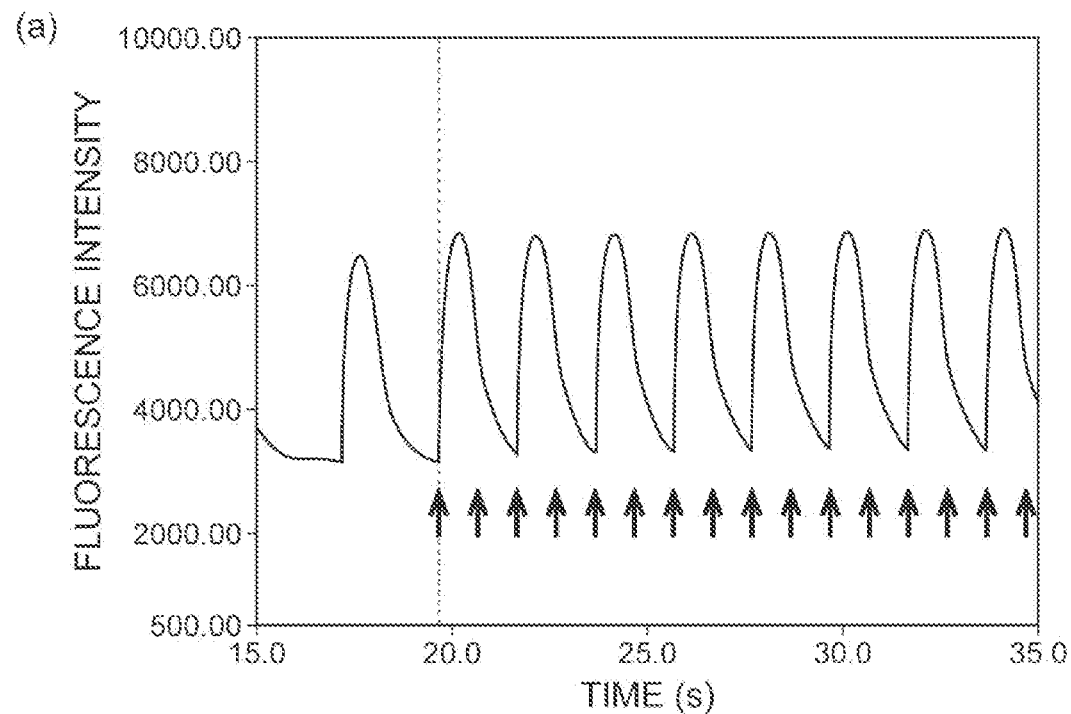
FIG. 17 includes (a) a graph illustrating a measurement result of a temporal variation of fluorescence intensity using an electrical stimulation device having an electrode of a coaxial cable shape in the related art, and (b) a graph illustrating a measurement result of a temporal variation of fluorescence intensity using a cell observation device 1 according to the embodiment.
Figure 17:
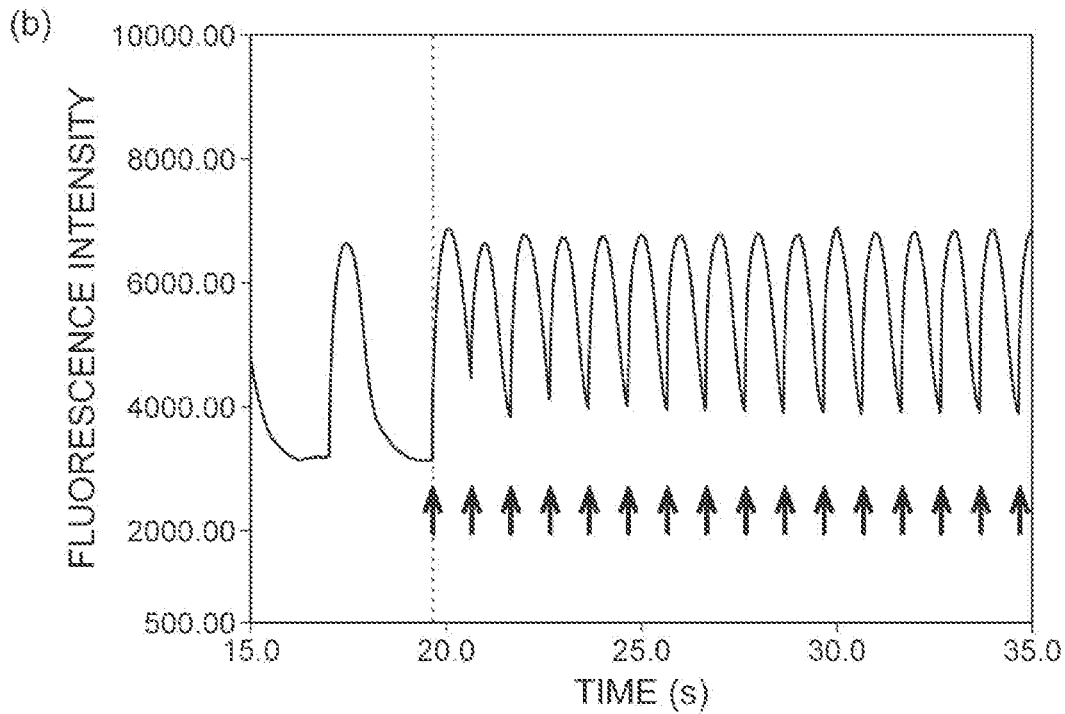

FIG. 17 illustrates an example of a measurement result when myocardial cells which are differentiated from iPS cells are observed using a microplate 20 in which the cross-section of the bottom of the well 21 in the depth direction has a U shape. The myocardial cells are dyed with $Ca^{2+}$-sensitive pigment. A portion (a) in FIG. 17 illustrates a measurement result of a temporal variation of the fluorescence intensity with a variation in $Ca^{2+}$ concentration in the cells when electrical stimulation of 1.0 Hz is applied to the cells using the electrical stimulation device having electrodes of a coaxial cable shape in the related art. A portion (b) in FIG. 17 illustrates a measurement result of a temporal variation of the fluorescence intensity with a variation in $Ca^{2+}$ concentration in the cells when electrical stimulation of 1.0 Hz is applied to the cells using the cell observation device 1 having a structure in which the first electrode 17a disposed close to the center of the well 21 extends more than the second electrode 17b in a state in which the electrode pair 17 is disposed in the well 21 having a U shape. As can be seen from the portion (a) in FIG. 17, the variation in fluorescence intensity in response to application of electrical stimulation (where a dotted line in the drawing indicates an application start timing and an arrow in the drawing indicates application timings of 1.0 Hz) could not be observed when the electrode structure according to the related art is used. On the other hand, as can be seen from the portion (b) in FIG. 17, the variation in fluorescence intensity in response to application of electrical stimulation (where a dotted line in the drawing indicates an application start timing and an arrow in the drawing indicates application timings of 1.0 Hz) could be observed when the electrode structure according to the this embodiment is used. From the above-mentioned measurement results, it can be seen that when cells are observed using the microplate 20 in which the bottom face of the well 21 has a concave shape such as a U shape, the first electrode 17a disposed close to the center extends more than the second electrode 17b and it is thus possible to reduce the distance between the sample S located on the bottom face of the well 21 and the tip of the first electrode 17a and thus to efficiently apply electrical stimulation to the sample S.

The present invention is not limited to the above-mentioned embodiments.

Figure 18:
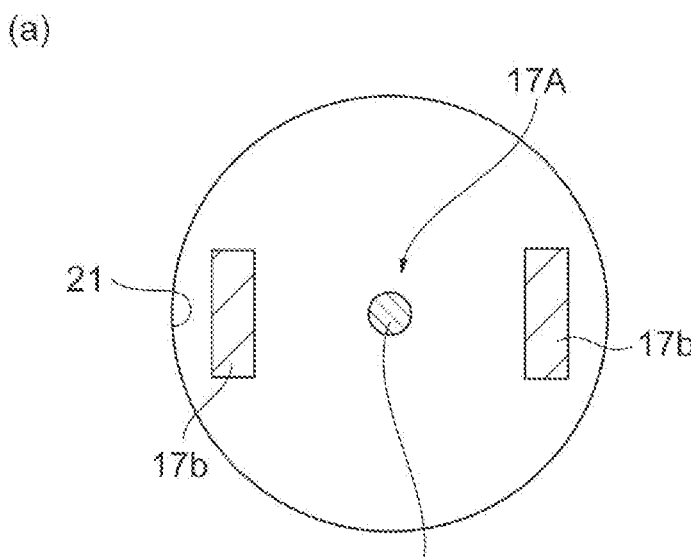
FIG. 18 is a cross-sectional view illustrating a structure of an electrode pair 17A according to a modified example of the embodiment.
Figure 18:
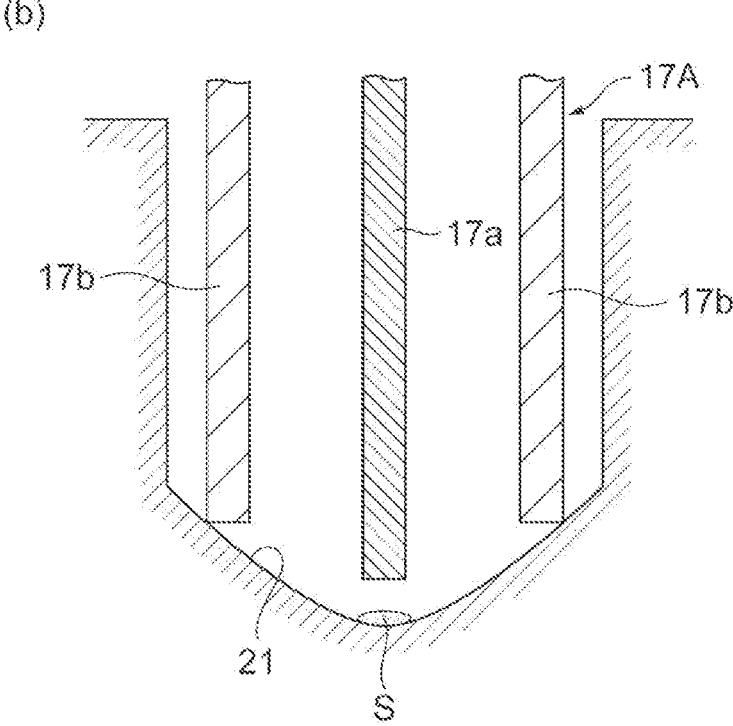
Figure 19:
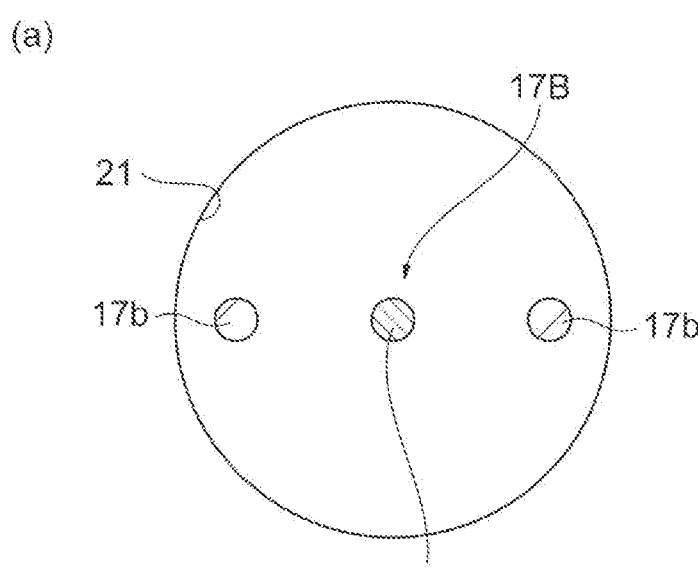
FIG. 19 is a cross-sectional view illustrating a structure of an electrode pair 17B according to a modified example of the embodiment.
Figure 19:
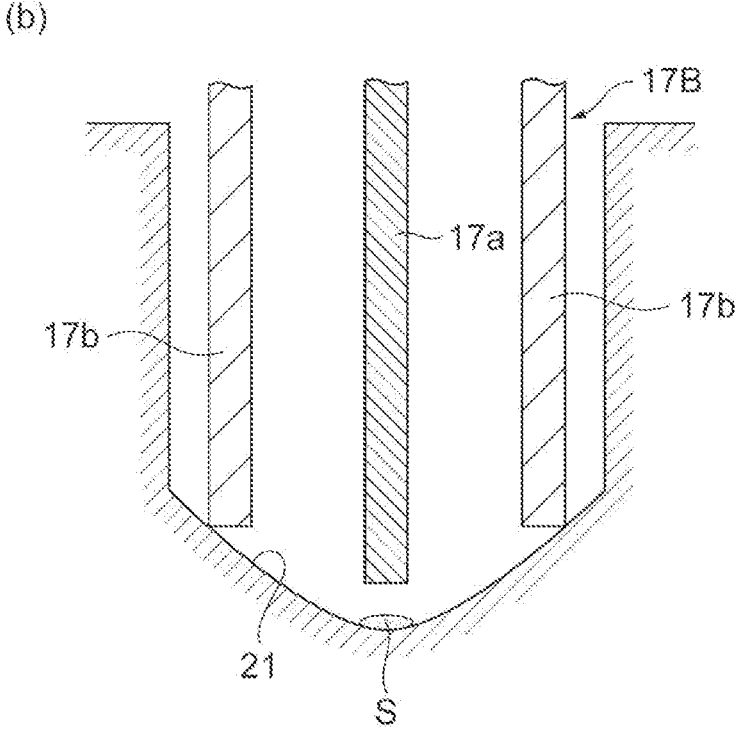

For example, the structure of the electrode pair 17 of the electrical stimulation unit 16 in the cell observation devices 1 and 1A is not limited to the tubular shape, but may employ various shapes. FIG. 18 illustrates a configuration of an electrode pair 17A according to a modified example of the present invention in a state in which the electrode pair is inserted into a well 21 of the microplate 20, where a portion (a) in FIG. 18 is a cross-sectional view taken along the opening of the well 21 and a portion (b) in FIG. 18 is a cross-sectional view taken along the depth direction of the well 21. As illustrated in the drawing, the second electrode 17b is formed of two plate-shaped electrodes which are disposed in parallel to each other and the first electrode 17a may be a rod-shaped electrode (for example, a columnar electrode) which is disposed along the second electrode between the two plate-shaped electrodes. FIG. 19 illustrates a configuration of an electrode pair 17B according to another modified example of the present invention in a state in which the electrode pair is inserted into a well 21 of the microplate 20, where a portion (a) in FIG. 19 is a cross-sectional view taken along the opening of the well 21 and a portion (b) in FIG. 19 is a cross-sectional view taken along the depth direction of the well 21. As illustrated in the drawing, the second electrode 17b is formed of two rod-shaped electrodes (for example, columnar electrodes) which are disposed in parallel to each other and the first electrode 17a may be a rod-shaped electrode (for example, a columnar electrode) which is disposed along the second electrode between the two plate-shaped electrodes. In the electrode pairs 17A and 17B, the first electrode 17a may have a prism shape, may have a plate shape, or may be coated with an insulator.

Figure 20:
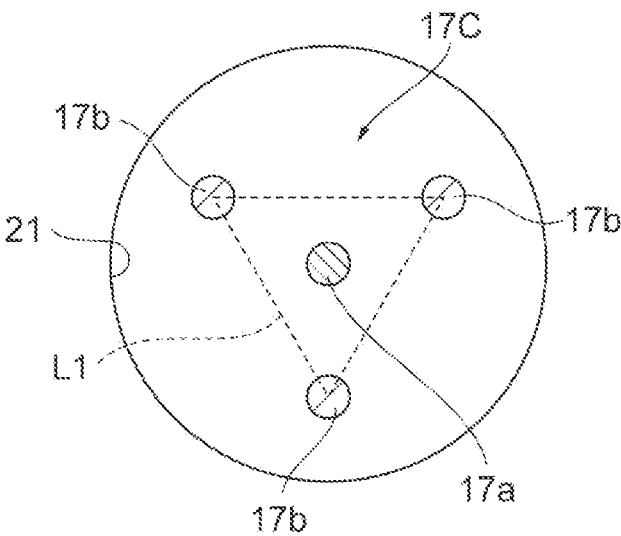
FIG. 20 is a cross-sectional view illustrating a structure of an electrode pair 17C according to a modified example of the embodiment.

FIG. 20 is a cross-sectional view taken along the opening of a well 21 in a state in which an electrode pair 17C according to another modified example of the present invention is inserted into the well 21 of the microplate 20. Like the electrode pair 17C illustrated in the drawing, three or more second electrodes 17b may be provided. The electrode pair 17C includes three rod-shaped second electrodes 17b which are arranged in parallel to each other and a rod-shaped first electrode 17a which is disposed between the second electrodes 17b. Specifically, the first electrode 17a is disposed at the center of an area which is surrounded with boundary lines L1 connecting the centers of the cross-sections of the second electrodes 17b taken along the opening of the well 21.

Figure 21:
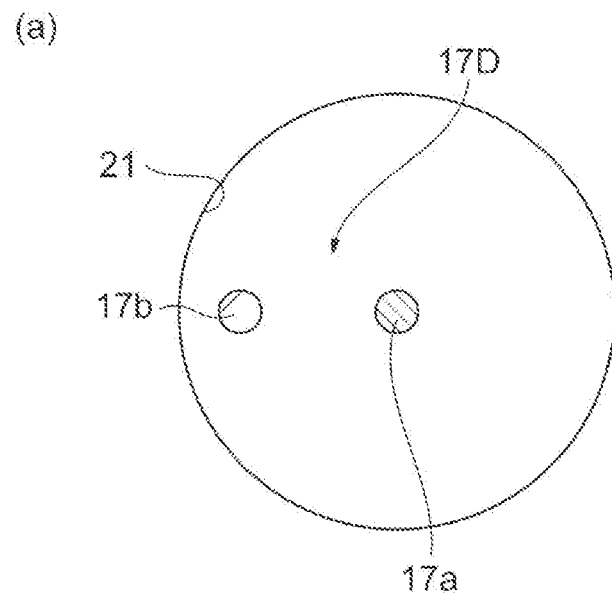
FIG. 21 is a cross-sectional view illustrating a structure of an electrode pair 17D according to a modified example of the embodiment.
Figure 21:
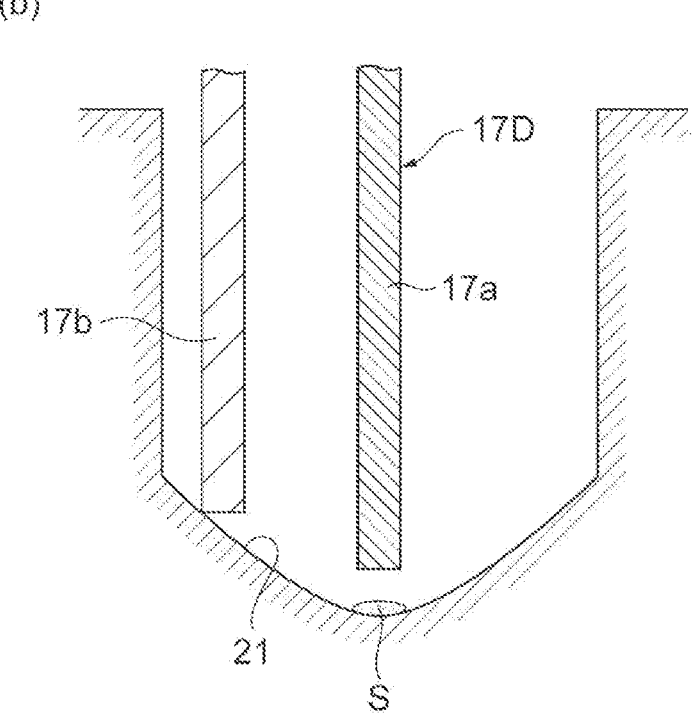
Figure 22:
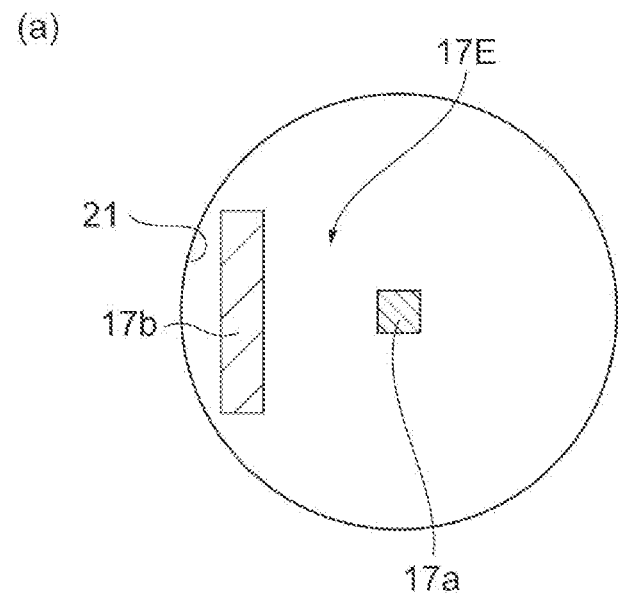
FIG. 22 is a cross-sectional view illustrating a structure of an electrode pair 17E according to a modified example of the embodiment.
Figure 22:
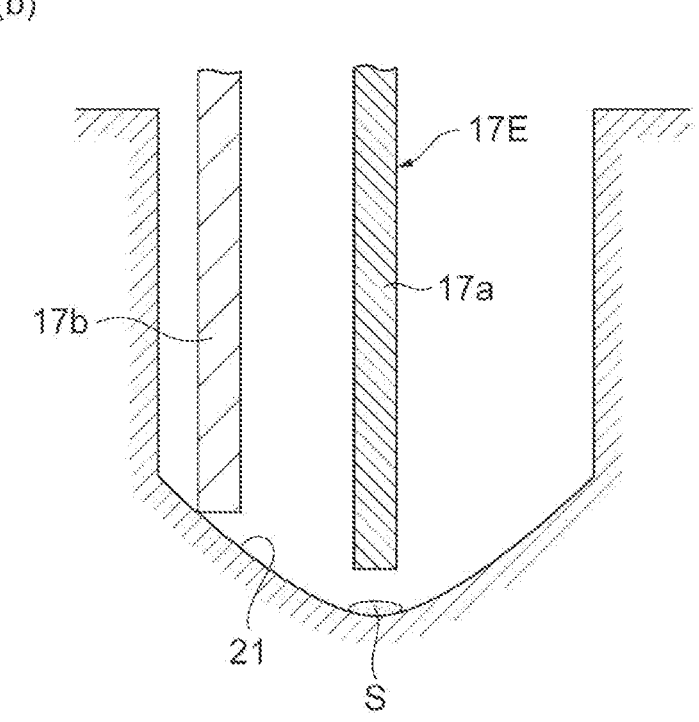

FIG. 21 illustrates a configuration of an electrode pair 17D according to another modified example of the present invention in a state in which the electrode pair is inserted into a well 21 of the microplate 20, where a portion (a) in FIG. 21 is a cross-sectional view taken along the opening of the well 21 and a portion (b) in FIG. 21 is a cross-sectional view taken along the depth direction of the well 21. As illustrated in the drawing, the second electrode 17b may be formed of one rod-shaped electrode (for example, an electrode having a columnar shape or a prism shape) and the first electrode 17a may be formed of a rod-shaped electrode (for example, an electrode having a columnar shape or a prism shape) which is disposed close to the center of the well 21 in parallel to the second electrode 17b. FIG. 22 illustrates a configuration of an electrode pair 17E according to another modified example of the present invention in a state in which the electrode pair is inserted into a well 21 of the microplate 20, where a portion (a) in FIG. 22 is a cross-sectional view taken along the opening of the well 21 and FIG. a portion (b) in FIG. 22 is a cross-sectional view taken along the depth direction of the well 21. As illustrated in the drawing, the second electrode 17b may be formed of one plate-shaped electrode and the first electrode 17a may be formed of a rod-shaped electrode (for example, an electrode having a columnar shape or a prism shape) which is disposed close to the center of the well 21 in parallel to the second electrode 17b. These electrode pairs 17D and 17E are employed in a case in which the number of wells 21 formed in the microplate 20 is equal to or greater than 100 such as 364 and the width of the well 21 is small. When the electrode pairs 17D and 17E are used in this case, the electrode pairs can be easily inserted into the well 21 and the tip of the first electrode 17a can be easily disposed close to the center of the bottom face of the well 21.

Figure 23:
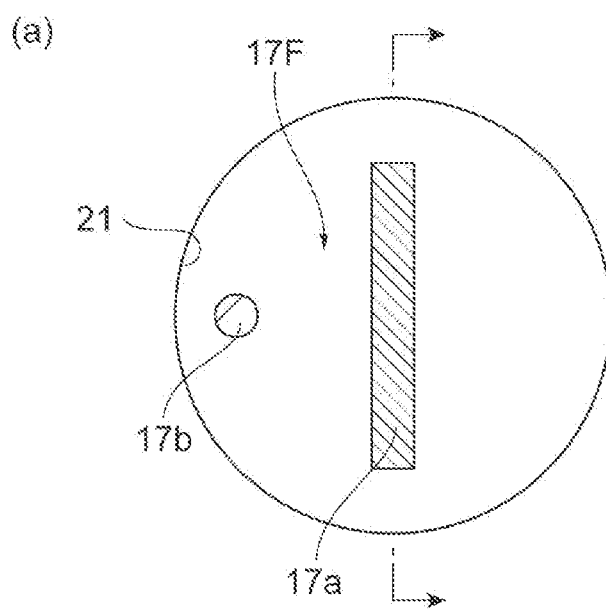
FIG. 23 is a cross-sectional view illustrating a structure of an electrode pair 17F according to a modified example of the embodiment.
Figure 23:
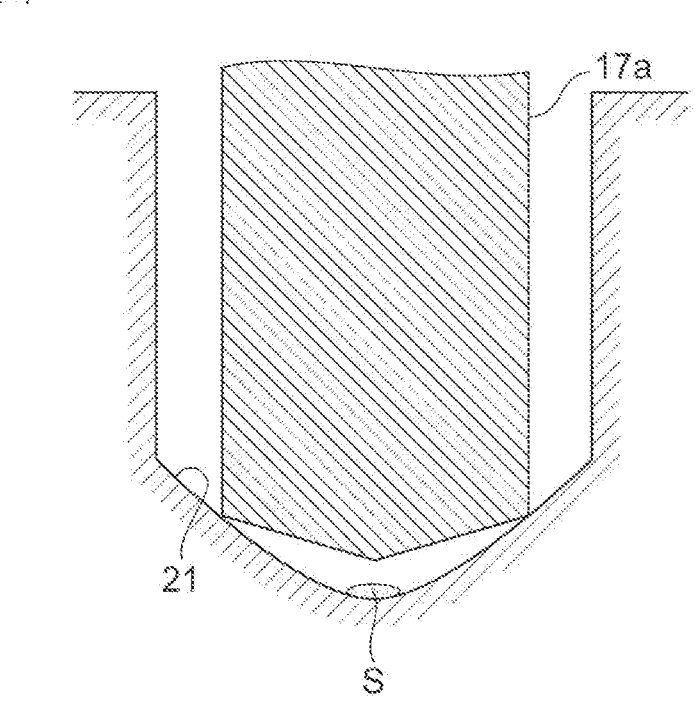
Figure 24:
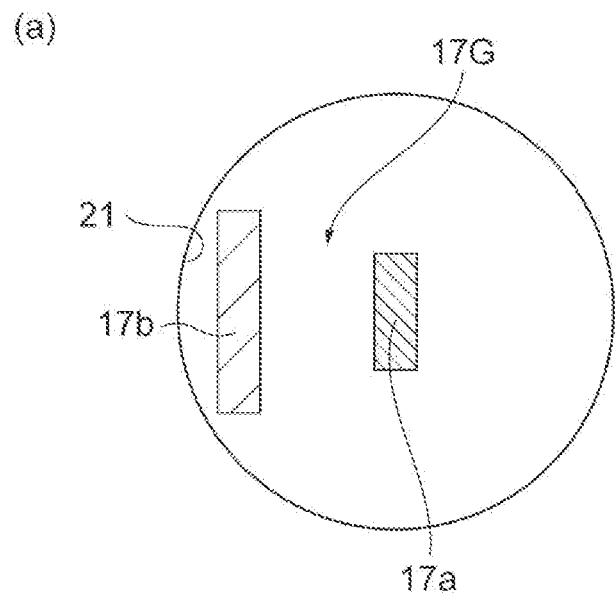
FIG. 24 is a cross-sectional view illustrating a structure of an electrode pair 17G according to a modified example of the embodiment.
Figure 24:
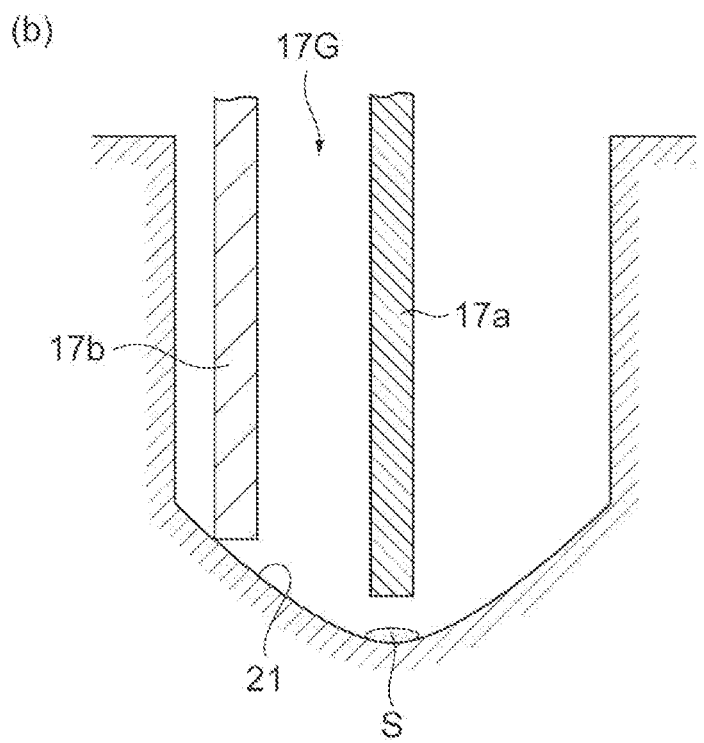

Here, the electrode pairs 17A to 17E which are employed by the cell observation device 1 have a structure in which the tip of the first electrode 17a extends more than the tip of the second electrode 17b. In the electrode pairs 17 and 17A to 17E, when the first electrode 17a is formed of a plate-shaped electrode, it is preferable that the width of the tip of the first electrode 17a be set to be smaller than the width of the tip of the second electrode 17b. FIGS. 23 and 24 illustrate the configurations of electrode pairs 17F and 17G according to modified examples of the present invention in a state in which the electrode pairs are inserted into the wells 21 of the microplate 20 in this case, where a portion (a) in FIG. 23 and a portion (a) in FIG. 24 are cross-sectional view taken along the opening of the well 21 and a portion (b) in FIG. 23 and a portion (b) in FIG. 24 are cross-sectional views taken along the depth direction of the well 21. The electrode pair 17G includes a first electrode 17a and a second electrode 17b which are plate-shaped electrodes, and the width of the first electrode 17a is set to be smaller than the width of the second electrode 17b. In the electrode pair 17F, the second electrode 17b is formed of a rod-shaped electrode, the first electrode 17a is formed of a plate-shaped electrode, the width of the first electrode 17a decreases toward the tip, and a convex portion having a width smaller than that of the tip of the second electrode 17b is formed at the tip of the first electrode 17a. According to the electrode pairs 17F and 17G having this configurations, it is possible to easily reduce the distance between the sample S held on the concave bottom face 22 of the well 21 and the first electrode 17a.

Here, in the above-mentioned cell observation device or the above-mentioned electrical stimulation device, the second electrode may have a tubular shape and the first electrode may be disposed in the second electrode. According to this configuration, when the electrode pair is disposed in the holding unit of the sample case, it is possible to easily fit the shape of the electrode pair to the concave internal shape of the holding unit and to easily reduce the distance between the sample held on the bottom of the holding unit and the first electrode. As a result, it is possible to efficiently apply electrical stimulation to the sample.

The second electrode may include a plurality of electrode members and the first electrode may be disposed between the plurality of electrode members. According to this configuration, it is possible to easily decrease the size of the electrode pair and to appropriately apply electrical stimulation to the sample in the holding unit.

The first electrode may have a pillar shape. In this case, it is possible to easily reduce the distance between the sample held on the bottom of the holding unit and the first electrode. As a result, it is possible to efficiently apply electrical stimulation to the sample.

The width of the tip of the first electrode may be set to be smaller than the width of the tip of the second electrode.

17

18

According to this configuration, it is possible to easily reduce the distance between the sample held on the concave bottom of the holding unit and the first electrode. As a result, it is possible to efficiently apply electrical stimulation to the sample.

INDUSTRIAL APPLICABILITY

The present invention is used for the cell observation device, the electrical stimulation device, and the cell observation method that can observe a reaction of a simple including cell to electrical stimulation and has enabled electrical stimulation to be appropriately applied to a cell disposed in the holding unit.

REFERENCE SIGNS LIST 17, 17A-17G electrode pair; 1, 1A cell observation device; 10 data acquiring device; 11 microplate holder (mounting unit); 12 microplate carrying mechanism; 16, 16A electrical stimulation unit (electrical stimulation device); 17a first electrode; 17b second electrode; 19 moving mechanism; 20 microplate (sample case); 21 well (holding unit); 22 bottom face; 30 position controller (position control unit); 32 imaging controller; 34 electrical stimulation controller; 40 moving image acquiring unit; 50 computer; 51 data analyzing unit; 52 control unit; 71 position adjusting mechanism (position adjusting unit); 72a, 72b support; 73 adjustment unit; S sample

The invention claimed is:

1. A system for observing a cell comprising:
a sample case including at least one holder;
a dark box configured to accommodate the sample case including the at least one holder holding a sample including the cell, wherein the sample case having a bottom portion that is formed of a material which can transmit light from the sample;
a light-guiding optical system including a lens, the light-guiding optical system disposed under the bottom portion of the sample case and configured to guide a two-dimensional image;
a camera configured to capture the two-dimensional image that is guided by the light-guiding optical system and output movie data of the two-dimensional image;
an electrical stimulator including an electrode pair having a first electrode and a second electrode, wherein the electrode pair is disposed in the holder; and
a computer configured to set an analysis area on the two-dimensional image and analyze optical intensity in the analysis area,
wherein the electrode pair has a structure in which a tip of the first electrode on a bottom side of the holder extends more than a tip of the second electrode on the bottom side of the holder, and
wherein the electrode pair is positioned by bringing the tip of the second electrode into contact with a bottom face of the holder and by allowing a space between the tip of the first electrode and the bottom face of the holder, when the electrode pair is inserted into the holder.

2. The system according to claim 1,
wherein the electrical stimulator is configured to repeatedly stimulate the sample with a cycle between 1 Hz to and 10 Hz.

3. The system according to claim 1,
wherein the first electrode and the second electrode are plate-shaped electrodes.

4. The system according to claim 1,
wherein the first electrode is disposed in a state in which the tip of the first electrode is separated by a predetermined distance from the bottom face of the holder.

5. The system according to claim 1, further comprising a light source configured to apply excitation light to the sample.

6. The system according to claim 5,
wherein the light-guiding optical system is configured to guide the excitation light from the light source to the sample.

* * * * *